(12) United States Patent
Culbertson et al.

(10) Patent No.: US 11,923,062 B2
(45) Date of Patent: *Mar. 5, 2024

(54) METHODS AND SYSTEMS FOR ANALYZING ACCESSING OF DRUG DISPENSING SYSTEMS

(71) Applicant: Protenus, Inc., Baltimore, MD (US)

(72) Inventors: Nicholas T. Culbertson, Baltimore, MD (US); Robert K. Lord, Baltimore, MD (US); Christopher David Jeschke, Pasadena, MD (US); Cosme Adrover, Cantonsville, MD (US)

(73) Assignee: Protenus, Inc., Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/172,381

(22) Filed: Feb. 22, 2023

(65) Prior Publication Data
US 2023/0207089 A1 Jun. 29, 2023

Related U.S. Application Data

(63) Continuation of application No. 17/652,349, filed on Feb. 24, 2022, now Pat. No. 11,621,065, which is a continuation of application No. 17/105,404, filed on Nov. 25, 2020, now Pat. No. 11,295,844, which is a continuation of application No. 16/436,643, filed on Jun. 10, 2019, now Pat. No. 11,282,597, which is a continuation-in-part of application No. 15/078,736, filed on Mar. 23, 2016, now Pat. No. 10,679,737.
(Continued)

(51) Int. Cl.
*G16H 40/67* (2018.01)
*G06Q 30/018* (2023.01)
*G16H 10/60* (2018.01)
*G16H 20/13* (2018.01)
*G16H 40/20* (2018.01)
*G16H 50/20* (2018.01)

(52) U.S. Cl.
CPC ......... *G16H 20/13* (2018.01); *G06Q 30/0185* (2013.01)

(58) Field of Classification Search
CPC .......................... G16H 20/13; G06Q 30/0185
See application file for complete search history.

(56) References Cited

U.S. PATENT DOCUMENTS 8,578,500 B2   11/2013   Long
8,793,790 B2    7/2014   Khurana et al.
(Continued)

OTHER PUBLICATIONS

Extended European Search Report issued in EP Appl. 20822602.7 dated Jun. 9, 2022.

*Primary Examiner* — Maroun P Kanaan
(74) *Attorney, Agent, or Firm* — Bookoff McAndrews, PLLC

(57) ABSTRACT

Various aspects described herein relate to presenting drug dispensing information. Data related to a plurality of dispensing events initiated by one or more employees, of an electronic drug dispensing system can be received. A set of dispensing events of the plurality of dispensing events can be determined as constituting possible misappropriation of drugs by the one or more employees. An alert related to the set of dispensing events can be provided based on determining that the set of dispensing events constitute possible misappropriation of drugs.

20 Claims, 17 Drawing Sheets

Related U.S. Application Data

(60) Provisional application No. 62/139,494, filed on Mar. 27, 2015.

(56) References Cited

U.S. PATENT DOCUMENTS

| | | |
|---|---|---|
| 9,202,189 B2 | 12/2015 | Long |
| 9,330,134 B2 | 5/2016 | Long et al. |
| 11,037,666 B1 | 6/2021 | Benoit et al. |
| 2004/0162740 A1 | 8/2004 | Ericsson et al. |
| 2009/0018882 A1 | 1/2009 | Burton et al. |
| 2010/0268157 A1 | 10/2010 | Wehba |
| 2011/0264459 A1* | 10/2011 | Tyler .................. G06Q 30/0185 |
| | | 707/E17.014 |
| 2011/0288886 A1* | 11/2011 | Whiddon ................ G16Z 99/00 |
| | | 705/3 |
| 2012/0289787 A1 | 11/2012 | Kurgan et al. |
| 2013/0091539 A1 | 4/2013 | Khurana et al. |
| 2013/0173309 A1 | 7/2013 | Dworkin |
| 2015/0205954 A1 | 7/2015 | Jou et al. |
| 2015/0235334 A1 | 8/2015 | Wang |
| 2015/0269824 A1 | 9/2015 | Zhang |
| 2015/0381631 A1 | 12/2015 | Salem et al. |
| 2016/0085986 A1 | 3/2016 | Long |
| 2016/0180022 A1 | 6/2016 | Paixao |
| 2016/0267224 A1* | 9/2016 | Natarajan ............... G16H 10/60 |
| 2017/0272336 A1 | 9/2017 | Johnstone et al. |
| 2018/0039736 A1 | 2/2018 | Williams |
| 2018/0174673 A1 | 6/2018 | Defrank et al. |
| 2019/0139638 A1 | 5/2019 | Keefe et al. |

* cited by examiner

FIG. 5

Return to Dashboard | YOU SEARCHED FOR Patient name Frank McDaniel from 10/24/13 - 05/12/14

Patient Summary — 502

- NAME Frank McDaniel
- DOB 12/13/1963   51 years old
- MRN JH37708860
- ADDRESS 7147 Colonial Rd Drum, MD 21292
- PHONE 410-695-0277
- INSURANCE Humana
- PCP Lorraine Bailey

Employee's Information

- NAME Jane McDaniel
- USERNAME JMCDANI1
- EMAIL jmcdani1@jhmi.edu
- PHONE 410-874-4563
- DEPARTMENT Pediatric Clinic
- AFFILIATION Staff
- TITLE Registered Nurse
- ADDRESS 1106 Annapolis Rd. Baltimore, MD 21223

EMPLOYEE WORKFLOW

| | |
|---|---|
| Physician | |
| CLINIC NAME | |
| Records Clerk | |
| Insurance Specialist | |
| ORTHOPEDIC CLINIC | |
| Registered Nurse | 508 |
| Physicians Assistant | |
| Medical Assistant | |
| CLINIC NAME | |
| Patient Coordinator | |
| Pathology Tech | |
| Registered Nurse | 510 |
| MEDICINE SERVICE | |
| Receptionist | |
| Medical Assistant | |
| Registered Nurse | |

506 · 504

Oct 24  Nov 13  Dec 3  Dec 23  Jan 12  Feb 1  Feb 21  Mar 13  Apr 2  Apr 22  May 12

| DATE & TIME | MODULE — 512 | ACTION | NOTES |
|---|---|---|---|
| 2/28/15 @ 9:31 AM | Patient Lookup Encounter | Viewed | Aenean lacinia bibendum nulla sed consectetur. |

Return to Dashboard

YOU SEARCHED FOR  Employee  named  Rhonda W.  from  10/24/13 - 05/12/14

Employee's Workflow — 702

NAME
Rhonda W.

AVG. TIME IN RECORDS
2min 35sec

AVG. RECORDS VIEWED PER DAY
8

LAST PATIENT VIEWED
Frank McDaniel

LAST ACTION TAKEN
Viewed patient lookup schedule

TIME SPENT IN PATIENT RECORD
1min 54sec

Patient Summary

NAME
Frank McDaniel

DOB
12/13/1963 - 51 years old

MRN
JH37708860

ADDRESS
7147 Colonial Rd
Drum, MD 21292

PHONE
410-695-0277

INSURANCE
Humana

PCP
Lorraine Bailey

704 → (Mitchell Martell)
706 → (Frank McDaniel)

| Name | Oct 24 | Nov 13 | Dec 3 | Dec 23 | Jan 12 | Feb 1 | Feb 21 | Mar 13 | Apr 2 | Apr 22 | May 12 |
|---|---|---|---|---|---|---|---|---|---|---|---|
| Mitchell Martell | | ● | | | | | | | | | |
| Frank McDaniel | ⑤ | | | | | | | | | | |
| Sam McMitchem | ③ | | | | | | | | | | |
| Nick Offerman | | | ② | | | | | | | | |
| Brian Ohare | | ⑩ | | | | | | | | | |
| Stella Onkle | | ②••• | | | | | | | | | |
| Jake O'Niel | | | | ㉞ | | | | | | | |
| Abraham Osprey | ⑤ | | | | | | | | | | |
| Bill Richardson | | | | | ⑩ | | | | | | |
| Amanda Rickson | | | ⑬ | | | | | | | | |
| Vlada Rumkanova | | | ② | | | | | | | | |
| Ira Ty-Ron Rollins | | | | | | | | | | | |
| Maria Sinclair | | | | | | | | ⑦ | | | |
| Peter Sinclair | | | | | | | | | | | |
| Janet Talbertson | | | | | | | | | ⑧ | | |
| Ralph Wiggum | | | | | | | | | | ⑨ | |

708

| DATE & TIME | MODULE | ACTION | NOTES |
|---|---|---|---|
| 11/13/14 @ 10:11 AM | Patient Lookup Schedule | Viewed | Curabitur blandit tempus porttitor. |
| 10/01/14 @ 9:21 AM | Report | Viewed | Maecenas sed diam eget risus varius blandit sit. |

800

802

- EMPLOYEE CHECKED PATIENTS WITH SAME FULL NAME
- EMPLOYEE CHECKED PATIENTS WITH SAME ADDRESS
- EMPLOYEE CHECKED PATIENTS EMPLOYED BY SAME HEALTHCARE PROVIDER NETWORK
- EMPLOYEE CHECKED PATIENTS WITH SAME LAST NAME
- PEDIATRICS EMPLOYEE CHECKED PATIENTS OLDER THAN 22
- EMPLOYEE USED UNUSUAL WORKSTATION
- EMPLOYEE ACCESSED UNUSUAL ENCOUNTER DEPARTMENT
- EMPLOYEE PRESENTED AN UNUSUAL ACTIVITY FOR 15 MINUTES

804

- SUSPICIOUS IF EMPLOYEE HAS NO PREVIOUS HISTORY OF ACCESSES TO PATIENT
- CLUSTERING OF ALL EMPLOYEES THAT HAVE CHECKED ANY PATIENT IN COMMON WITH EMPLOYEE
- SUSPICIOUS IF EMPLOYEE AND EMPLOYEES THAT ALSO CHECKED PATIENT ARE IN DIFFERENT CLUSTERS

METHODS AND SYSTEMS FOR ANALYZING ACCESSING OF DRUG DISPENSING SYSTEMS

CLAIM OF PRIORITY UNDER 35 U.S.C. § 119

This application is a continuation of and claims the benefit of priority to U.S. Non-Provisional application Ser. No. 17/652,349, filed Feb. 24, 2022, which is a continuation of U.S. Non-Provisional application Ser. No. 17/105,404, filed Nov. 25, 2020, now U.S. Pat. No. 11,295,844, issued on Apr. 5, 2022, which is a continuation of U.S. Non-Provisional application Ser. No. 16/436,643, filed Jun. 10, 2019, now U.S. Pat. No. 11,282,597, issued on Mar. 22, 2022, which is a continuation-in-part of U.S. Non-Provisional application Ser. No. 15/078,736, filed Mar. 23, 2016, now U.S. Pat. No. 10,679,737, issued Jun. 9, 2020, which claims the benefit of priority to U.S. Provisional Application No. 62/139,494, filed Mar. 27, 2015, all of which are incorporated herein by reference in their entireties.

BACKGROUND

With the advent of electronic medical records, a patient's medical record can be accessible by various employees operating in a healthcare provider network. The nature of medical workflows is such that traditional role- or attribute-based access control for the medical records may not be feasible as the complexity of clinical care may result in various parties needing to access a patient's medical record, and indeed, rigid access controls may prevent access in emergency situations. Accordingly, however, a given patient's medical record may be subject to breach, or inappropriate accessing, by various parties. A multitude of scenarios for breach can be envisioned where an employee may access a medical record of someone with whom they have a personal interest (e.g., a celebrity, family member, co-worker, etc.) who may be under the care of the healthcare provider network, where the access is unrelated to the employee actually providing services to that person in the healthcare industry. Not only is inappropriate accessing generally not desirable, but it can also result in fines to the healthcare provider network. Accordingly, it is in the healthcare provider network's interest to prevent inappropriate accessing of electronic medical records. Moreover, patients who feel their medical records are being compromised are much less likely to divulge truthful medical information to the healthcare provider network, and thus patient care may be impacted in this regard.

Auditing systems have been developed for tracking employee access of medical records, but these systems do not provide certain desirable analyses of the accessing.

In addition, electronic medical records can be used to operate or authorize operation of electronic drug dispensing systems. For example, electronic drug dispensing systems can be deployed at medical centers (e.g., on hospital floors, doctor's offices, etc.), and medical center personnel can operate the electronic drug dispensing systems to dispense certain drugs for certain patients. The electronic drug dispensing systems may dispense drugs for an identified patient based on a doctor's order accessed from an electronic medical record, and may log what drugs are dispensed for the patient, the quantity of drugs dispensed, the time/date of dispensing, etc.

The medical center personnel typically handle the drugs from the electronic drug dispensing system to the patient's location. In addition, in some cases, the medical center personnel may "waste" drugs, which can refer to a process of accounting for unused or mishandled drugs, that are to be disposed of. This process of "wasting" typically requires a witness to sign or acknowledge the "wasting." There are many points of potential misappropriation of drugs obtained from electronic drug dispensing systems.

Auditing systems have been developed for tracking drugs dispensed via drug dispensing systems, but these systems do not provide certain desirable analyses of the use and/or disposition of the dispensed drugs.

SUMMARY

The following presents a simplified summary of one or more aspects in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

In accordance with an aspect described herein a method for presenting electronic patient data accessing information is provided. The method includes receiving data related to a plurality of access events, by one or more employees, of electronic patient data, determining a set of access events in the plurality of access events constitute, by the one or more employees, possible breach of the electronic patient data, and providing an alert related to the set of access events based on determining that the set of access events constitute possible breach of the electronic patient data.

In another aspect, an apparatus for presenting electronic patient data accessing information. The apparatus includes at least one processor configured to perform various operations. The at least one processor can be configured to receive data related to a plurality of access events, by one or more employees, of electronic patient data, determine a set of access events of the plurality of access events constitute, by the one or more employees, possible breach of the electronic patient data, and provide an alert related to the set of access events based on determining that the set of access events constitute possible breach of the electronic patient data. The apparatus also includes a memory coupled to the at least one processor.

In yet another aspect, a non-transitory computer-readable medium storing computer executable code for presenting electronic patient data accessing information is provided. The code includes code for receiving data related to a plurality of access events, by one or more employees, of electronic patient data, determining a set of access events of the plurality of access events constitute, by the one or more employees, possible breach of the electronic patient data, and providing an alert related to the set of access events based on determining that the set of access events constitute possible breach of the electronic patient data.

In another aspect, a method for presenting drug dispensing information is provided. The method includes receiving data related to a plurality of dispensing events initiated by one or more employees, of an electronic drug dispensing system, determining a set of dispensing events in the plurality of dispensing events that constitute possible misappropriation of drugs from the electronic drug dispensing system by the one or more employees, and providing an alert related to the set of dispensing events based on determining that the set of dispensing events constitute the possible misappropriation of drugs.

In another aspect, an apparatus for presenting drug dispensing information includes at least one processor and a memory coupled to the at least one processor. The at least one processor is configured to receive data related to a plurality of dispensing events initiated by one or more employees, of an electronic drug dispensing system, determine a set of dispensing events in the plurality of dispensing events constitute possible misappropriation of drugs from the electronic drug dispensing system by the one or more employees, and provide an alert related to the set of dispensing events based on determining that the set of dispensing events constitute the possible misappropriation of drugs.

In another example, a non-transitory computer-readable medium storing computer executable code for presenting drug dispensing information is provided. The code includes code for receiving data related to a plurality of dispensing events initiated by one or more employees, of an electronic drug dispensing system, determining a set of dispensing events in the plurality of dispensing events constitute possible misappropriation of drugs from the electronic drug dispensing system by the one or more employees, and providing an alert related to the set of dispensing events based on determining that the set of dispensing events constitute the possible misappropriation of drugs.

To the accomplishment of the foregoing and related ends, the one or more aspects comprise the features hereinafter fully described and particularly pointed out in the claims. The following description and the annexed drawings set forth in detail certain illustrative features of the one or more aspects. These features are indicative, however, of but a few of the various ways in which the principles of various aspects may be employed, and this description is intended to include all such aspects and their equivalents.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIGS. 4-7 illustrate example graphical user interface (GUI) screens in accordance with aspects described herein.

FIG. 8 illustrates example rules, tags, or meta data in accordance with aspects described herein.

FIGS. 10-14 illustrate additional example graphical user interface (GUI) screens in accordance with aspects described herein.

DETAILED DESCRIPTION

Figure 1:
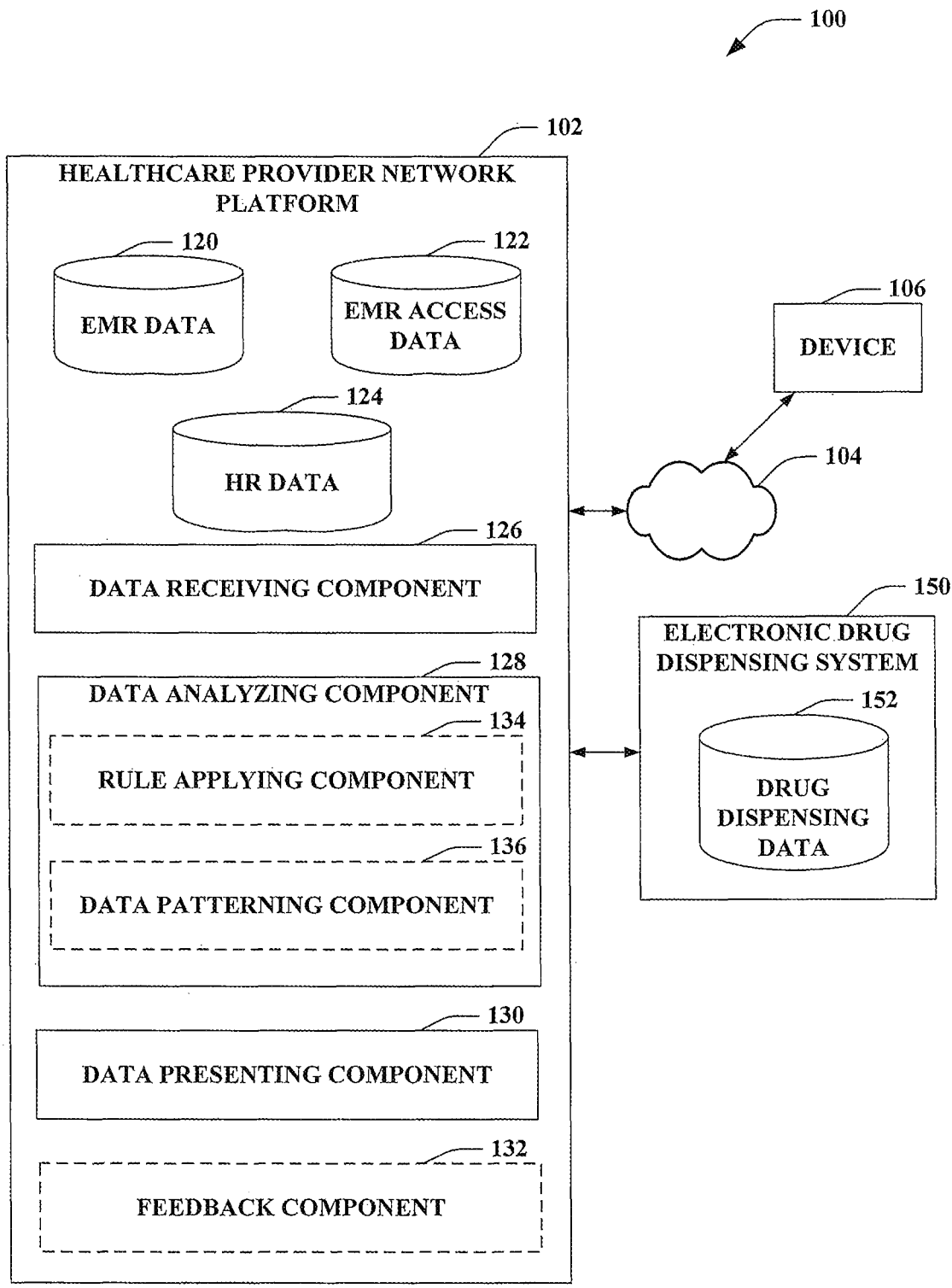
FIG. 1 illustrates an example system for presenting electronic patient data access data in accordance with aspects described herein.

Aspects described herein generally relate to collecting data from one or more entities in a healthcare provider network, and analyzing the data to determine possible inappropriate accessing of the data or misappropriation of drugs. For example, determining the possible inappropriate accessing (also referred to herein as "breach") of the data or misappropriation of drugs can be a manual or automated process based on other analysis of the data. For example, the collected data can include electronic patient data (e.g., from an electronic medical record (EMR)) and data related to accessing the electronic patient data (e.g., an identifier of an employee accessing the EMR data, a time of accessing the EMR data, etc.), data from an electronic drug dispensing system (e.g., dispensing data such as time of dispensing, amount of dispensing, type of drug dispensed, wasting activity, etc.). The data may also include human resources (HR) data that can indicate information related to the employees accessing the electronic patient data and/or dispensing the drugs. The collected data can be analyzed, as described herein, to detect whether one or more accesses of the data may possibly be a breach of the data, whether one or more dispensing of drugs is possibly for inappropriate purposes, etc. If possible breach or misappropriation is detected, one or more alerts can be generated (e.g., to one or more interfaces) for further investigation as to whether the access/dispensing is inappropriate given additional context around the access/dispensing. In another example, a representation of the collected data can be generated based on the analysis and provided to an interface to facilitate breach/misappropriation detection. Moreover, though EMR data is generally referred to herein, the concepts described can be applied to substantially any electronically stored patient data.

In one specific example, data received from the various sources can be analyzed based on rule-based analysis. In additional examples, the data can be analyzed based on one or more of clusterings of data (e.g., based on one or more determined relationships), machine-learning related to the data, network or other statistics analysis (e.g., Markov chains), etc. In this regard, in an example, one or more ontologies relating to the data can be generated to correlate the data such to enrich events being tracked with clinical context. For example, accesses of similar electronic patient data by different employees can be observed over time (e.g., based on statistical analysis) such to associate the different employees as part of a clinical care team. In this regard, in one example, access of a related EMR by an employee outside of the clinical care team may indicate a possible breach in accessing the EMR. Similarly, access of an EMR by an employee on the clinical care team without similar accessing by other members of the clinical care team may indicate possible breach in accessing the EMR. These example analyses combine and either add to or detract, with unequal weights, from the suspicious nature of event, and increase or decrease the probability that such events are a breach. In any case, when parameters from the data related to an access event achieve a threshold for possible breach, an alert can be generated for providing to an interface for managing compliance for further investigation. In addition, in an example, feedback regarding alerts can be received and utilized in determining thresholds for subsequent alerts such to allow for more or less conservative breach detection.

It is to be appreciated that each healthcare provider network and/or a related entity (e.g., hospital, doctor's office, etc.) may have a different workflow, and thus the analysis of the data in this regard facilitates providing customized breach detection for a given workflow. In a specific example, a hospital may employ a nurse anesthetist in the Operating Room who records the initiation of surgery, while another hospital might employ anesthesiologists who records the initiation of anesthesia. Additionally, in another specific example, some physicians may use phone or email to follow up with patients after an appointment and thus access patient data between appointments where other physicians might only access patient data while the patient is in clinic. Moreover, in another specific example, some clinics may use nurses in an administrative role (such as office assistant) whereas other clinics might use nurses in a research capacity similar to an academic physician, etc. In any case, analyzing the data using clustering, machine-learning, network or other statistical analysis, etc. allows for breach detection for a given workflow than more rigid strictly rule-based systems.

In another specific example, where data received from various sources is analyzed based on rule-based analysis, accesses of an electronic drug dispensing system by different employees can be observed over time (e.g., based on statistical analysis) to detect potential misappropriation of drugs from the electronic drug dispensing system. For example, log files from the electronic drug dispensing system may be analyzed to determine dispensing behavior, wasting behavior, etc. Certain types of drugs can trigger alerts for certain behavior. In other examples, statistical analysis can allow for discovering frequent wasting of certain specific drugs, types of drugs, etc. by an employee, by a department or team, etc. In any case, when parameters from the data related to an access event or multiple access events achieve a threshold for possible breach, an alert can be generated for providing to an interface for managing drug misappropriation for further investigation. In addition, in an example, feedback regarding alerts can be received and utilized in determining thresholds for subsequent alerts such to allow for more or less conservative misappropriation detection.

Various aspects are now described with reference to the drawings. In the following description, for purposes of explanation, numerous specific details are set forth in order to provide a thorough understanding of one or more aspects. It may be evident, however, that such aspect(s) may be practiced without these specific details.

As used herein, the term "determining" or "evaluating" encompasses a wide variety of actions. For example, "determining" and "evaluating" may include calculating, computing, processing, deriving, investigating, looking up (e.g., looking up in a table, a database or other data repository, or another data structure), ascertaining, and/or the like. Also, "determining," and "evaluating" may include receiving (e.g., receiving information), accessing (e.g., accessing data in a data repository), and/or the like. Also, "determining" may include resolving, selecting, choosing, establishing, and the like.

As used herein, the terms "element," "module," "component," and "system" may refer to a computer-related entity, either hardware, a combination of hardware and software, software, or software in execution. For example, a module may be, but is not limited to being, a machine-executable process running on a processor, a processor, an object, a thread of execution, a machine-executable program, and/or a computer. By way of illustration, both a process running on a server and the server may be a module or a component. One or more modules or components may reside within a process and/or thread of execution. In some implementations, a module may be localized on one computer and/or distributed among two or more computers.

It will be appreciated that, in accordance with one or more aspects described herein, inferences may be made regarding determining protocols to provide to the application, analyzing data for performance of the protocols, and/or the like, as described. As used herein, the term to "infer" or "inference" refers generally to the process of reasoning about or inferring states of the system, environment, and/or user from a set of observations as captured via events and/or data. Inference may be employed to identify a specific context or action, or may generate a probability distribution over states, for example. The inference may be probabilistic—that is, the computation of a probability distribution over states of interest based on a consideration of data and events. Inference may also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources.

Various aspects or features will be presented herein in terms of systems that may include a number of devices, components, modules, and the like. It is to be understood and appreciated that the various systems may include additional devices, components, modules, etc. and/or may not include all of the devices, components, modules, etc., discussed in connection with the figures. A combination of these approaches may also be used.

Figure 2:
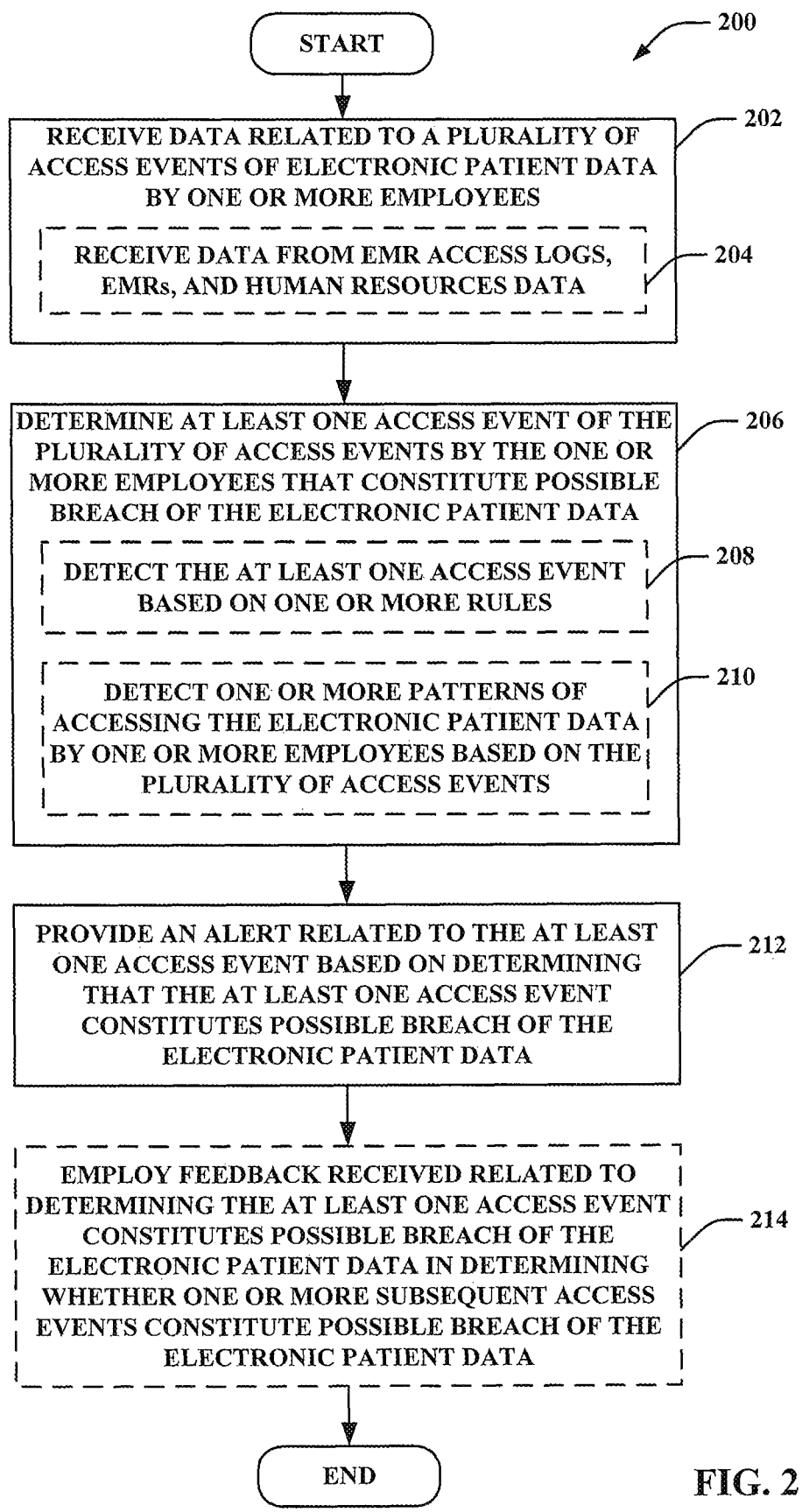
FIG. 2 illustrates an example method for presenting electronic patient data access data in accordance with aspects described herein.
Figure 3:
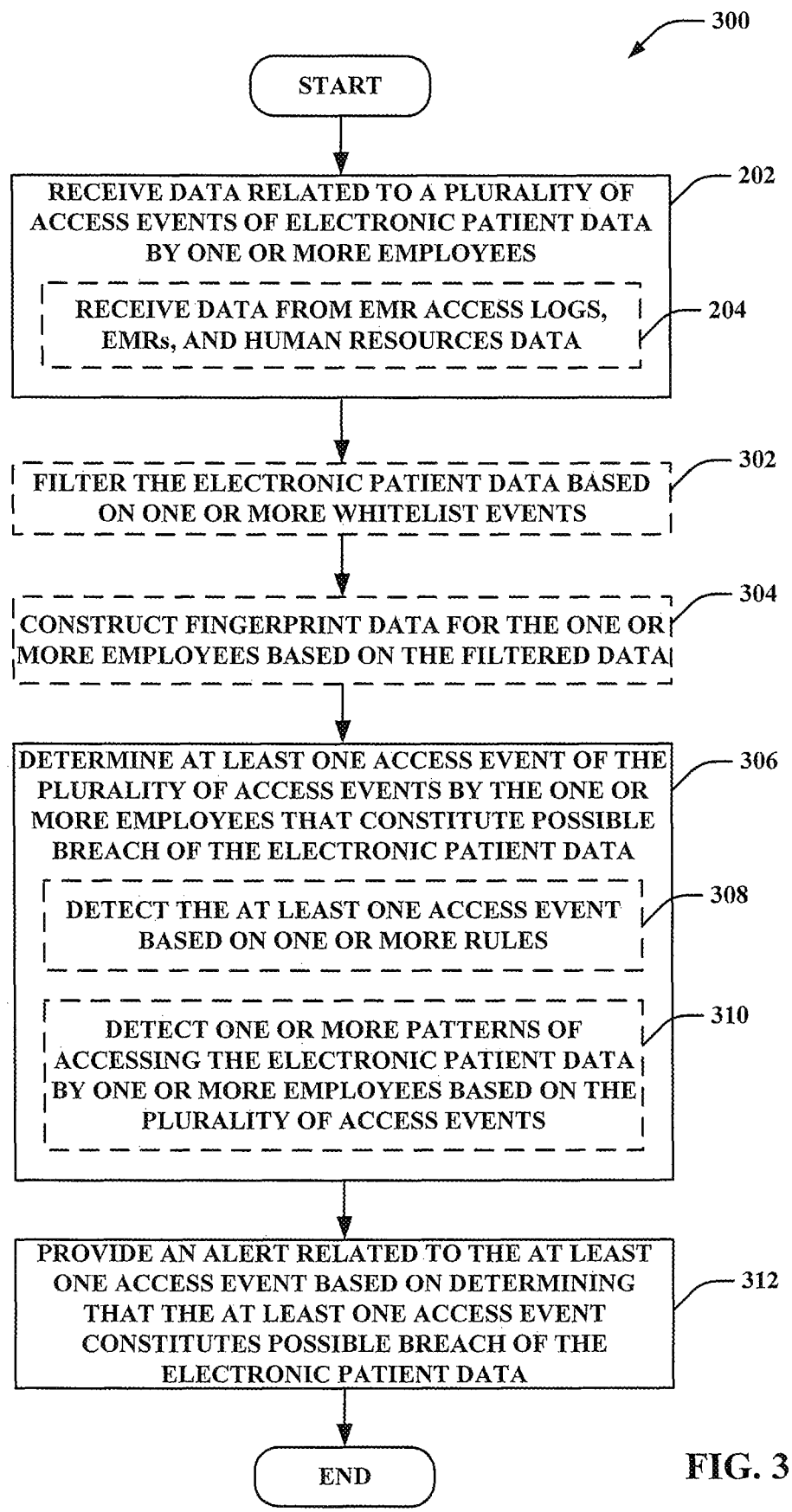
FIG. 3 illustrates an example method for presenting electronic patient data access data in accordance with aspects described herein.
Figure 9:
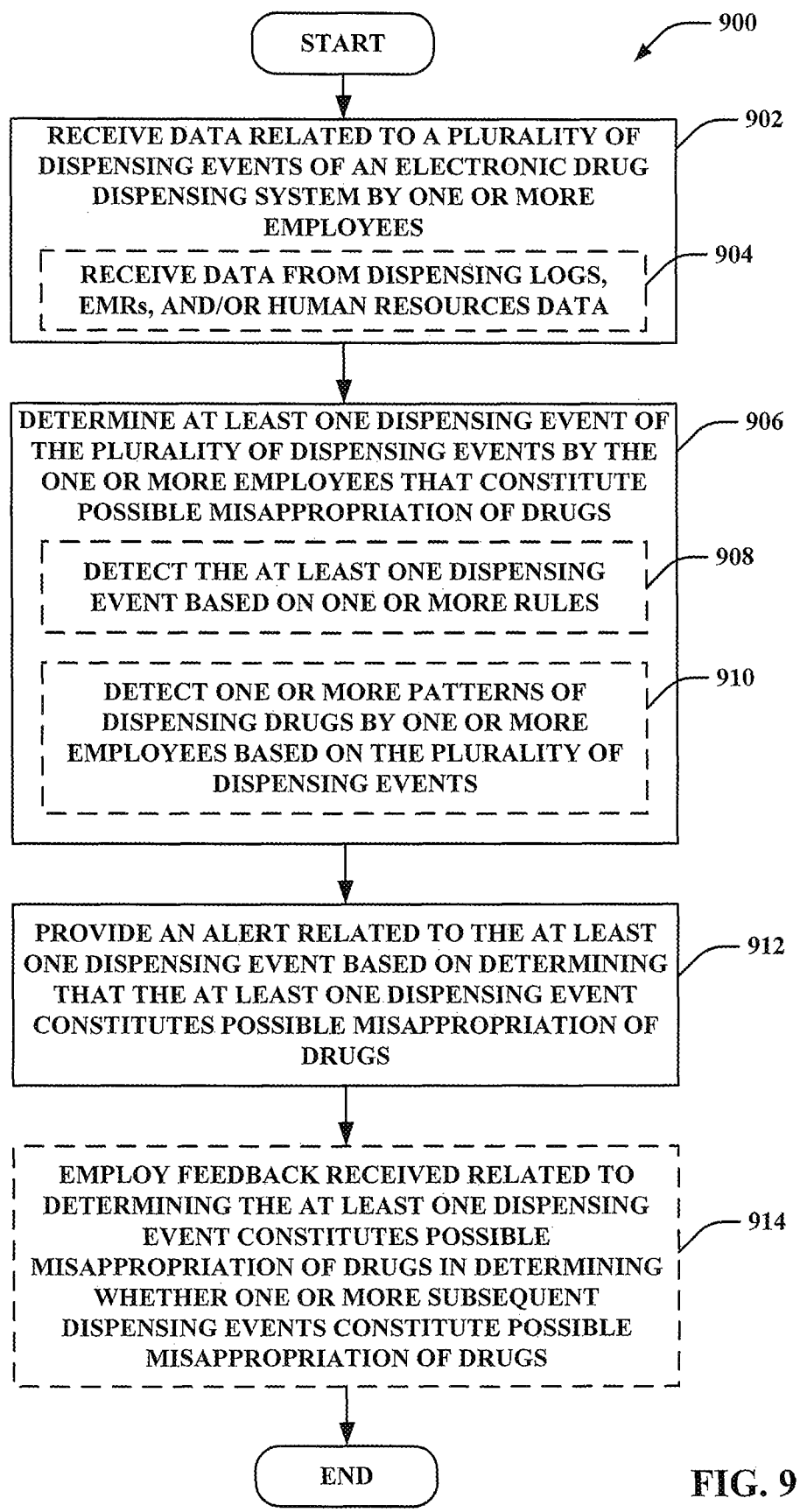
FIG. 9 illustrates an example method for presenting drug dispensing data in accordance with aspects described herein.

Referring to FIGS. 1-3 and 9, aspects are depicted with reference to one or more components and one or more methods that may perform the actions or functions described herein. Although the operations described below in FIGS. 2-3 and 9 are presented in a particular order and/or as being performed by an example component, it should be understood that the ordering of the actions and the components performing the actions may be varied, depending on the implementation. Moreover, it should be understood that the following actions or functions may be performed by a specially-programmed processor, a processor executing specially-programmed software or computer-readable media, or by any other combination of a hardware component and/or a software component capable of performing the described actions or functions.

Referring to FIG. 1, an example system 100 is illustrated that facilitates processing EMR access data to determine one or more possible breaches of EMR data and/or processing drug dispensing data to determine one or more possible misappropriations of drugs. System 100 includes a healthcare provider network platform 102 for storing and facilitating viewing, modifying, etc. EMRs relating to one or more patients currently or previously in (or scheduled for) care of a healthcare provider network (e.g., hospital, doctor's office, imaging center, laboratory, etc.) related to the healthcare provider network platform 102. Healthcare provider network platform 102 can communicate over a network 104 (e.g., a local area network (LAN), Internet, etc.) with one or more other nodes, such as device 106, to allow accessing of the healthcare provider network platform 102 to view one or more EMRs, analyze accessing of EMRs, etc.

Healthcare provider network platform 102 includes EMR data 120 (and/or more generally electronic patient data), which may include a plurality of EMRs and/or other data related to a plurality of patients. The EMR data 120 can indicate demographic information regarding a patient (e.g., name, address, phone number, gender, date of birth, etc.) as well as medical history information regarding the patient (e.g., symptoms, diagnoses, allergies, conditions, etc.). The medical history information can relate to current or previous (or scheduled) care with the healthcare provider network. EMRs can be stored electronically such to facilitate electronic access thereto for viewing, modifying, etc. the information related to a given patient. This can improve convenience of accessing the information, but can also present security concerns related to accessing the information. For example, as described, restricting access to EMRs for certain employees of the healthcare provider network can be impractical in a clinical care setting especially in emergency situations. Thus, various employees of the healthcare provider network may have unrestricted access to EMRs (or at least access that errs on the side of more information to account for situations where more data may be needed to provide adequate healthcare). This can lend to inappropriate accessing of EMRs such to determine protected information regarding certain patients. For example, an employee may seek medical history information for a celebrity, family member, or other person of interest though the access of information may be unrelated to care of the patient by the employee. Accordingly, healthcare provider network platform 102 can facilitate detection of various possible inappropriate data accesses (e.g., breaches) of the EMR data 120.

Healthcare provider network platform 102 can also include EMR access data 122, which may include one or more access logs that indicate time, type, employee, etc. related to accessing EMR data 120, and human resources (HR) data 124 for the employees of the healthcare provider network that indicate personal information for the employees, such as name, address, phone number, position, department, etc. In an example, the employees of the healthcare provider network may also include contract employees (e.g., insurance billers), research employees, etc., that may not necessarily be directly connected to care of a patient. The EMR data 120, EMR access data 122, and/or HR data 124 may be analyzed together to determine possible breaches in accessing the EMR data 120. Moreover, though shown as part of the healthcare provider network platform 102, it is to be appreciated that a portion or all of EMR data 120, EMR access data 122, and/or HR data 124 can exist in one or more other platforms or systems, and may be imported to or otherwise accessed by healthcare provider network platform 102 for analyzing EMR accesses.

Healthcare provider network platform 102 can also include a data receiving component 126 for receiving at least one of the EMR data 120, EMR access data 122, and/or HR data 124, a data analyzing component 128 for analyzing the received data to detect one or more possible breaches of the EMR data 120, and a data presenting component 130 for presenting the analyzed data, the one or more possible breaches, etc. Healthcare provider network platform 102 may also optionally include a feedback component 132 for receiving feedback regarding a detected possible breach for use by data analyzing component 128 in detecting one or more subsequent possible breaches of the data. Data analyzing component 128 may optionally include a rule applying component 134 for applying one or more rules to detect a possible breach in the data, and/or a data patterning component 136 for detecting one or more patterns in the data, which may be used to determine one or more possible breaches in the data. The various components of the healthcare provider network platform may be co-located within a system or network, and/or may be distributed among various systems and/or networks that can communicate with one another (e.g., via network 104 or other networks).

In an additional or alternative example, the healthcare provider network platform 102 may include or otherwise interface with one or more electronic drug dispensing systems 150, which may also be referred to as an automatic dispensing cabinet (ADC). For example, the electronic drug dispensing systems 150 may store drugs for dispensing to patients of the healthcare provider network (e.g., patients in hospital rooms, out-patients in doctors' offices, etc.). A healthcare professional may access an electronic drug dispensing system 150 to obtain drugs prescribed for a given patient to administer the drugs to that patient. In an example, the electronic drug dispensing system 150 may provide an interface for the healthcare professional to identify the patient and request the drugs listed on the prescription. The electronic drug dispensing system 150 may provide the healthcare professional with access to one or more drugs based on a request. In one example, the electronic drug dispensing system 150 may interface with EMR data 120 or an associated application to obtain or modify patient information, prescription information, patient diagnosis information, etc., which can also be used in authorizing and/or logging drug dispensing. Moreover, in an example, the electronic drug dispensing system 150 may interface with HR data 124 to obtain healthcare professional employment information, security profiles, etc., which can also be used in authorizing and/or logging drug dispensing.

The electronic drug dispensing system 150 may include some drug securing features, such as compartments for one or more specific drugs to prevent obtaining drugs that are not part of an associated prescription, a dispensing feature to control the number of drugs dispensed for a given request (e.g., based on the prescription or otherwise), etc. Moreover, in an example, the electronic drug dispensing system 150 and/or healthcare provider network platform 102 can provide a process for "wasting" drugs dispensed by the electronic drug dispensing system 150. For example, where drugs are dispensed by not given to the patient (which may be for substantially any reason, such as patient refusal, drug contamination, etc.), electronic drug dispensing system 150 and/or healthcare provider network platform 102 can allow for creating an event indicating that the drug was dispensed but not used (and indeed disposed of). The event may also require a witness to approve the event before the event is processed. In any case, drug dispensing data 152 can be logged by the electronic drug dispensing system 150 (and/or by the healthcare provider network platform 102) to include drug dispensing information (e.g., a healthcare professional requesting dispensing, prescription/patient information, drug being dispensed, amount dispensed, wasting information, etc.).

In this regard, data receiving component 126 can also receive the drug dispensing data 152, and data analyzing component 129 can analyze the drug dispensing data to detect possible misappropriation of drugs. For example, rule applying component 134 can apply one or more rules to the drug dispensing data 152 to detect possible misappropriation, data patterning component 136 can determine one or more patterns of dispensing and/or detect outlier dispensing activity, etc. Where possible misappropriation is detected, data presenting component 130 can present an alert on the interface to allow further investigation (e.g., within the drug dispensing data 152 or other offline investigation). In addition, in an example, feedback component 132 can allow for specifying validity of a detected misappropriation for refining future misappropriation detection processes.

FIG. 2 illustrates an example method 200 for processing electronic patient data access data to determine possible breaches in accessing EMRs. Method 200 includes, at Block 202, receiving data related to a plurality of access events of electronic patient data by one or more employees. Data receiving component 126 can receive data related to the plurality of access events of electronic patient data by one or more employees. This can optionally include, at Block 204, receiving data from EMR access logs, EMRs, and human resources data. Thus, for example, data receiving component 126 can receive data from EMR access logs (e.g., EMR access data 122), EMRs (e.g., EMR data 120), and human resources data (e.g., HR data 124). As described, data receiving component 126 may receive this data from one or more data sources in a healthcare provider network and/or other system or network, which may be distributed across one or more networks, co-located, etc.

Method 200 also includes, at Block 206, determining at least one access event of the plurality of access events by the one or more employees that constitute possible breach of the electronic patient data. Data analyzing component 128 can determine the plurality of access events by the one or more employees that constitute possible breach of the electronic patient data. For example, this can optionally include, at Block 208, detecting the at least one access event based on one or more rules. Data analyzing component 128 may include rule applying component 134 for detecting the at least one access event based on the one or more rules. In one example, rule applying component 134 can apply one or more rules to the data using a rules-based mechanism to determine the at least one access event constituting the possible breach. For instance, the one or more rules may relate to detecting common data among EMR access data 122 and HR data 124. In a specific example, rules applying component 134 may apply one or more rules to the EMR access data 122 relating to determining whether an employee accessing an EMR has similar personal information as a patient to which the EMR corresponds based on additionally acquiring EMR data 120 and HR data 124 (e.g., similar last names, addresses, phone numbers, etc.). In one example, rule applying component 134 may additionally apply filtering rules in this example, to prevent excessive false positives (e.g., for common last names). In any case, in this example, data analyzing component 128 may determine a possible breach in the electronic patient data, which may be presented to an interface as described herein for further investigation.

In another example, the one or more rules may relate to determining whether data relating to a position of the employee from HR data 124 (e.g., or inferred through other data, such as determining a synthetic department of the employee as described further below) corresponds to care of the patient based on the EMR data 120. For instance, the one or more rules may relate to determining whether a pediatric employee (e.g., physician, nurse, administrative assistant, etc.) accesses an EMR of an older patient (e.g., based on an age of the patient according to the EMR data 120), as this may constitute a possible breach in accessing the EMR data 120. For example, one or more such rules may be based on a position and/or department (e.g., rules may be present for administrative assistants, but perhaps not for doctors, and/or may relate to whether patient care based on the EMR data 120 corresponds to a department of the employee based on HR data 124). Thus, in one example, a cardiology administrative assistant accessing a patient EMR with no cardiac symptom or condition history may result in detecting a possible breach in the data. In an example, rule applying component 134 may apply multiple rules in detecting a possible breach (e.g., similar last name between employee and patient along with the fact that the employee has not provided care to the patient based on the EMR data 120).

It is to be appreciated that rule applying component 134 may apply the one or more rules to filter the data for possible breaches, and the possible breaches may further be analyzed based on patterning, as described below, and/or the data may be analyzed based instead on patterning without applying the one or more rules described above. In another example, the one or more rules may relate to the patterned data, and thus rule applying component 134 may apply one or more rules to patterned data determined by data patterning component 136 to detect possible breach.

In any case, determining the at least one access event that constitute possible breach of the electronic patient data may additionally or alternatively optionally include, at Block 210, detecting one or more patterns of accessing the electronic patient data by one or more employees based on the plurality of access events. Data analyzing component 128 may include data patterning component 136 for detecting one or more patterns of accessing the electronic patient data by one or more employees based on the plurality of access events. For example, data patterning component 136 may detect the one or more patterns at least in part by clustering the data related to accessing of the electronic patient data based on detecting commonalities in the data, machine-learning commonalities in the data, network analyzing commonalities in the data (e.g., generating Markov chains), etc. The commonalities can be determined based on computing statistical inferences such that data commonalities are meaningful. For instance, data patterning component 136 may detect patterns by a given employee (e.g., typical EMR accessing times by the employee), patterns for groups of employees (e.g., determining that a group of employees typically access the same medical record, which may be in a given order or otherwise), etc. In an example, in this regard, data analyzing component 128 may determine the at least one access that constitute possible breach of the electronic patient data based at least in part on detecting that the at least one access is inconsistent with the one or more patterns determined by the data patterning component 136.

In a specific example, data patterning component 136 may detect, based on the EMR access data 122, that an employee typically accesses EMRs in the EMR data 120 very quickly (e.g., opens access and closes access of the EMR within 1 minute). Accordingly, data analyzing component 128 may determine whether EMR access data 122 includes one or more accesses by the employee that achieve a threshold duration over the normal (or computed average) for the employee, which may indicate a possible breach in accessing the EMR data 120 by the employee (e.g., when analyzed with other patterns and/or rules applied to the data). In another specific example, data patterning component 136 may detect that accesses by the employee according to the EMR access data 122 typically occur at a given workstation in the healthcare provider network (e.g., based on an identifier, network address, etc. related to the workstation), and data analyzing component 128 may determine whether the EMR access data 122 includes one or more accesses by the employees from a different workstation, which may indicate a possible breach.

In another specific example, data patterning component 136 may generate one or more patterns regarding employee transitions between EMR accesses for one or more patients (e.g., in one or more departments, etc.). In this example, data analyzing component 128 may detect transitions from one EMR access action to another in a given department (e.g., an office assistant who frequently schedules patients moving to an action of adding information to a patient's EMR) that are of low probability given an individually fit gamma distribution for the employee, that are detected to be outside of a defined number of standard deviations beyond a mean value for the employee, etc. For example, it is to be appreciated that the number of standard deviations may be specified by an administrator or other user account of the healthcare provider network platform 102 (e.g., per a given employee, group or type of employees, all employees, etc.) or otherwise configured to achieve a desired level of possible breach detection. More generally, data patterning component 136 can generate fingerprints of detected behavior patterns for one or more employees based on analyzing the EMR access data 122 in this regard, and data analyzing component 128 can determine EMR accesses that are outside of the fingerprints. For example, data patterning component 136 can generate fingerprints based at least in part on mathematically representing and characterizing the EMR access data for the given employee to detect typical patternable EMR access behavior by the employee. In addition, in an example similar to the rules-based example described above for an employee accessing an EMR for a patient related to a department (or having a condition relating to a department) inconsistent with the employee's department, it may be possible that the employee accesses such EMRs outside of the department regularly as part of her/his employment. Thus, in an example, data patterning component 136 may additionally or alternatively determine that an employee typically accesses EMRs corresponding to one or more departments (e.g., regardless of a department for the employee in HR data 124), and data analyzing component 128 may detect a possible breach where the employee accesses EMR(s) outside of the detected one or more departments for which the employee typically accesses EMRs.

In another specific example, data patterning component 136 may detect accessing of certain EMRs in the EMR data 120 by a group of employees based on the EMR access data 122. For example, data patterning component 136 may determine that a certain one or more doctors, assistants, nurses, administrative assistants, etc. typically access the same EMRs, which may indicate these employees as part of a clinical care group. Accordingly, data analyzing component 128 may determine whether EMR access data 122 indicates accesses to EMRs by a portion of the employees in the group but not by another portion, which may indicate a possible breach. For example, this may be based on a time of the accessing according to the EMR access data 122, such that an access by a portion of the employees in a group that is not within a threshold time of access by the other portion of the employees in the group may indicate a possible breach. In another example, data analyzing component 128 may determine whether EMR access data 122 indicates accesses to an EMR by the group and a corresponding access to the EMR by another employee that is not in the group, which may indicate a possible breach.

It is to be appreciated that data patterning component 136 can constantly or periodically generate the one or more patterns such that the patterns can evolve over time based on changes to other data in the healthcare provider network platform 102 (e.g., addition, movement, removal, etc. of employees in the EMR access data 122 and/or HR data 124, etc.). Moreover, for example, EMR access data 122 can be periodically received in EMR data logs, received using a request/receive mechanism (e.g., file transfer protocol (FTP)), publish/subscribe mechanism, etc.).

Method 200 also includes, at Block 212, providing an alert related to the at least one access event based on determining that the at least one access event constitutes possible breach of the electronic patient data. Data presenting component 130 can provide the alert related to the at least one access event based on determining that the at least one access even constitutes possible breach of the electronic patient data. For example, data presenting component 130 can render the alert on an interface (e.g., a dashboard interface of alerts, a patient profile interface graphically depicting EMR access data 122 related to accessing the EMR, etc.), as described further herein. The alert may allow a professional to receive the alert and further investigate the alert to determine whether a possible breach of the data has occurred and/or to remediate the possible breach. In an example, the further investigation can be facilitated by indications on interfaces presented by the data presenting component 130 that relate to rules of rule applying component 134, data patterns from data patterning component 136, etc. as described further herein.

In addition, in an example, data analyzing component 128 may determine a confidence level or priority related to a detected possible breach, which may be based on which of the one or more rules the detected possible breach satisfies, which of the one or more patterns to which the detected possible breach relates, a level of deviation from the one or more patterns, and/or the like. In this example, data presenting component 130 may provide a representation of the access event along with any confidence or priority information.

Method 200 may optionally include, at Block 214, employing feedback received related to determining the at least one access event constitutes possible breach of the electronic patient data in determining whether one or more subsequent access events constitute possible breach of the electronic patient data. For example, feedback component 132 can receive and employ feedback related to determining the at least one access event constitutes possible breach of the electronic patient data in determining whether one or more subsequent access events constitute possible breach of the electronic patient data. In an example, feedback can be provided via one or more interfaces to indicate whether a possible breach detection is actually considered a breach, whether breach detection is too conservative, and/or whether more conservative breach detection is desired. Data analyzing component 128 can utilize the feedback information to automatically activate/deactivate one or more rules used by rule applying component 134, one or more patterns detected in the EMR access data 122 by data patterning component 136, one or more numbers of standard deviations for detecting possible breaches, etc. to achieve a desired level of consideration for determining whether accesses defined in the EMR access data 122 are possible breach of the EMR data 120.

FIG. 3 illustrates an example method 300 for processing EMR access data to determine possible breaches in accessing EMRs. Method 300 includes, at Block 202, receiving data related to a plurality of access events of electronic patient data by one or more employees. Data receiving component 126 can receive data related to the plurality of access events of electronic patient data by one or more employees, as described. This can optionally include, at Block 204, receiving data from EMR access logs, EMRs, and human resources data. Thus, for example, data receiving component 126 can receive data from EMR access logs (e.g., EMR access data 122), EMRs (e.g., EMR data 120), and human resources data (e.g., HR data 124). As described, data receiving component 126 may receive this data from one or more data sources in a healthcare provider network and/or other system or network, which may be distributed across one or more networks, co-located, etc.

Method 300 also optionally includes, at Block 302, filtering the electronic patient data based on one or more whitelist events. For example, data analyzing component 128 can filter the electronic patient data based on the one or more whitelist events. This may include filtering out the whitelist events as accesses to EMR data 120 (e.g., from the EMR access data 122) that are determined to not constitute a possible breach (e.g., legitimate authorized accesses of the EMR data 120). For example, data analyzing component 128 can determine the whitelist events from EMR access data 122 as accesses that demonstrate the employee has directly treated a patient corresponding to the EMR data being accessed and/or have contributed to their care. For example, whitelist events may include appointment entry, an entry related to ordering a procedure or medication for the patient, an update to allergy information, a patient check-in, a modification to primary care provider, etc. Thus, for example, accessing of EMR data in EMR access data 122 around these whitelist events may be filtered out. For example, this may lessen processing burden for determining possible breaches from the EMR access data 122, as described further below, as statistical processing, pattern detection, etc. can occur on a subset of the entire EMR access data 122 having filtered out the whitelist events. A non-exhaustive list of example whitelist events (which can also be referred to as "positive tags") that can be detected by data analyzing component 128 in the EMR access data 122 (e.g., by determining a type of the EMR access as specified in or otherwise determined based on the EMR access data 122) is provided below.

---

This employee entered allergy information for this patient.
This employee initiated an admission, discharge or transfer action for this patient.
This employee edited this patient's diagnoses.
This employee modified identity information in this patient's record.
This employee entered immunization information in this patient's record.
This employee reviewed and accepted this patient's medication history.
This employee created an order for this patient.
This employee discontinued an order for this patient.
This employee approved a medication order for this patient.
This employee is the overall care provider.
This employee created a Procedure note for this patient.
This employee is a technologist who fulfilled an order.
This employee is involved with Radiology Information Systems.
This employee instantiated a procedure.
This employee cancelled something in the EMR.
This employee edited something in the EMR.
This employee edited the patient's emergency department disposition.
This employee is the patient's primary care physician (PCP).
This employee is labeled as the visit provider ID, indicating they are the attending provider for the patient's visit.
This employee closed the patient encounter.
This employee created an appointment for this patient.
This employee cancelled an appointment for this patient.
This employee checked in the patient to an appointment.
This employee created an after visit summary for this patient.
This employee created the patient encounter.
This employee updated the patient's allergies.
This employee created the user ID for the patient.
This employee last reviewed the patient's medications.
This employee reviewed the patient's problem list.
This employee edited the patient's diagnosis history.

-continued

This employee has sequentially viewed more than one patient with a similar name - but only explored one record extensively.
This employee accessed a patient's record with explicit permission from the compliance office.
This employee is a supervisor and is connected to this patient through a whitelisted subordinate.
This employee is a trusted user.
This employee is authorized to access this patient's data.

---

Method 300 also optionally includes, at Block 304, constructing fingerprint data for the one or more employees based on the filtered data. For example, data analyzing component 128 can construct the fingerprint data for the one or more employees based on the filtered data. For example, data analyzing component 128 may construct the fingerprint data to include, from the EMR access data 122, a collection list of daily encounters of one or more employees at the healthcare institution, a collection list of accesses of a patient EMR for multiple time periods occurring throughout the day (e.g., each 15 minute period of the day) or a daily list, a collection list of employee EMR accesses of patient EMRs for multiple time periods occurring throughout the day or a daily list, a collection list of patient encounters (e.g., all patient encounters, encounters within a period of time, etc.), a collection list of synthetic department accesses, and/or the like. For example, data analyzing component 128 may determine a synthetic department for an employee based at least in part on detecting a type of EMR data 120 that is most frequently accessed by the employee (e.g., intensive care unit (ICU), emergency department, etc.). Further processing can occur on one or more of the fingerprint data collections to determine possible breach of the electronic patient data (e.g., EMR data 120), as described herein.

Method 300 also includes, at Block 306, determining at least one access event of the plurality of access events by the one or more employees that constitutes possible breach of the electronic patient data. For example, data analyzing component 128 may determine the at least one access event of the plurality of access events by the one or more employees that constitutes possible breach of the electronic patient data. For example, data analyzing component 128 may analyze the fingerprint data for a given employee with whitelist events filtered out. As described, determining the at least one access event at Block 306 may optionally include, at Block 308, detecting the at least one access event based on one or more rules. For example, rule applying component 134 can apply one or more rules to the fingerprint data to determine whether an access is a possible breach, where the one or more rules may correspond to one or more tags defined for identifying in the fingerprint data. The tags, for example, may include negative tags that are indicative of possible breach and/or neutral tags that may not alone be indicative of possible breach, but may add information to an access identified as possible breach to indicate whether the access is more or less likely a breach of the EMR data 120.

As described herein the one or more rules/tags may include a plurality of detectable events in the data. A non-exhaustive list of example rules/tags and relevant determinations made by the data analyzing component 128 to apply the rule/tag to an EMR access in the fingerprint data is provided below.

| Rule/Tag | Relevant Determination |
| --- | --- |
| This employee viewed a record for a patient that has never visited the healthcare institution. | Analyze fingerprint data (e.g., patient encounter history) to determine if the patient has ever visited the healthcare institution. |
| This employee viewed a record with no clinical data. | Analyze the EMR to determine if clinical data exists. |
| This employee does not routinely work with other employees in this patient's record. | Hierarchical clustering of employees to determine if employee routinely works with other employees who access this patient's record. |
| This employee has never viewed this patient's medical record. | Analyze fingerprint data to determine employee/patient combination. |
| This employee viewed this patient's medical record outside of an encounter window. | Analyze fingerprint data (e.g., patient encounter history) to determine if the EMR access is a threshold of time after a last patient encounter. |
| This employee is not involved in the treatment of this patient. | Analyze fingerprint data to determine if employee has edited medical record to indicate they are providing direct care for this patient. |
| This employee has checked two patients with the same address. | Analyze fingerprint data to determine if two patients accessed by the employee have the same address (e.g., where the accesses occur within a threshold period of time, such as 1 day). |
| This employee shares the same last name as this patient. | Analyze fingerprint data (or access logs) to determine if a patient of an accessed EMR has the same last name as the employee. |
| This employee works in pediatrics and viewed an adult's record. | Analyze fingerprint data and HR data to determine accesses by the employee and the employee's department. |
| This employee is listed as an emergency contact in this patient's record. | Analyze fingerprint data and EMR data to determine if a patient of an accessed EMR has an emergency contact with the same name as the employee. |
| This employee works in a department that is not related to this patient's care. | Analyze fingerprint data and HR data to determine a history of associated departments of a patient EMR, and determine whether the employee is in one of the departments. |
| This employee viewed a medical record of a hospital employee. | Analyze fingerprint data and HR data (or access logs) to determine whether a patient of an accessed EMR is an employee (e.g. based on name, address, social security number, etc.). |
| This employee accessed this record from a workstation outside of their normal workflow pattern. | Analyze fingerprint data to determine normal workflow pattern of the employee (e.g., during a time period, as a sequence of accesses of different types and/or from different locations, etc.) to determine if workstation is outside the normal workflow. |
| This employee routinely times-out of sessions on public workstations. | Analyze fingerprint data to determine time periods associated with EMR accesses and/or a number of EMR accesses during which timeout occurred. |
| This employee generated a report outside of their normal workflow pattern. | Analyze fingerprint data to determine normal workflow pattern of the employee (e.g., during a time period, as a sequence of accesses of different types and/or from different locations, etc.) to determine if a generated report is contrary to the normal workflow. |
| This employee saved a report to a suspicious location on their computer. | Analyze fingerprint data to determine a save location of a report (e.g., as being in a location related to a personal storage device, such as an external memory card, cloud storage location, etc.). |
| This employee viewed this record outside of their normal work shift. | Analyze fingerprint data to determine EMR accesses outside of shift, where the shift can be determined by analyzing EMR accesses to determine a typical shift and/or HR data that may specify/track the shift. |
| This employee downloaded a large amount of patient data. | Analyze fingerprint data to determine a number of fingerprints over a period of time compared to a threshold, which may be a configured threshold and/or generated based on analyzing fingerprints to determine typical accesses by the employee over the period of time. |
| This employee printed a large amount of patient data. | Analyze fingerprint data to determine a number of fingerprints related to printing over a period of time compared to a threshold (e.g., a configured or generated threshold, as described above). |
| This employee accessed a record for a patient who is deceased. | Analyze fingerprint data (or access logs) to determine if an access is for an EMR of a deceased patient. |

-continued

| Rule/Tag | Relevant Determination |
|---|---|
| This employee is an OB-GYN professional checking a male patient. | Analyze fingerprint data, EMR data, and HR data (or access logs) to determine that the patient related to the accessed EMR is male, and a department of the employee as OB-GYN. |
| This employee accessed a record for a patient who lives near the employee. | Analyze fingerprint data, EMR data, and HR data to determine an address of the patient related to the accessed EMR and an address of the employee, and determine whether the addresses are within a threshold proximity. |
| This employee has accessed a patient's record that has been dormant for a period of time. | Analyze fingerprint data (e.g., a list of patient accesses) to determine if there are any accesses of the EMR within the period of time (e.g., 1 year). |
| This employee accessed a record for a patient that has not had an encounter within a period of time. | Analyze fingerprint data (e.g., patient encounter data) to determine if there are any patient encounters within the period of time (e.g., the last 60 days). |
| This employee is registered as "inactive" by the institution. | Analyze HR data to determine if employee accessing the EMR is "inactive." |
| This employee is not listed as assigned to one of the departments this patient visited. | Analyze fingerprint data and HR data to determine if employee accessing the EMR is not assigned to a department the patient visited. |
| This employee is a student who accessed another student's patient data. | Analyze fingerprint data and HR data (or access logs) to determine if the employee is a student and if the patient related to the EMR is a student. |
| This employee is checking their own medical record. | Analyze fingerprint data (and HR data) to determine if the employee and the patient related to the EMR are the same person. |
| This employee checks two patients with the exact same full name. | Analyze fingerprint data to determine if patients related to different EMR accesses by the employee (e.g., within a period of time) have the same full name. |
| This patient's condition is atypical for this employee's access history. | Analyze fingerprint data (e.g., patient encounter data) to determine typical access history and conditions associated with the patient EMRs to determine if this access is for a different condition that is not typically accessed by the employee. |
| This employee created a large number of reports on this date. | Analyze fingerprint data to determine whether a number of reports exceeds a threshold. |
| This employee was logged into multiple work stations at this time. | Analyze fingerprint data to detect multiple EMR accesses in overlapping periods of time. |
| This employee has sequentially viewed more than one patient with a similar name - and continued to explore both patients records. | Analyze fingerprint data to detect accessing by the employee of EMRs of patients having a similar name (e.g., same last name) within a period of time of each other. |
| This employee normally views a specific age group that this patient does not fit into. | Analyze fingerprint data to determine typical access history and ages associated with the patient EMRs to determine if this access is for a patient of a different age (e.g., exceeding a threshold difference of a typical age). |
| This employee accessed patient data for a potential VIP. | Determine VIPs based on searching local or national news feeds, encyclopedia websites, etc. for names and/or events (e.g., that the VIP may be in care of a healthcare provider), and analyze fingerprint data to detect access of the VIP EMR (e.g., based on name/location matching). |
| This employee accessed patient data on a subordinate or manager. | Analyze fingerprint data and HR data to determine accessing of a patient EMR corresponding to a subordinate or manager. |

Rule applying component 134 can apply one or more of these rules/tags to the at least one event (e.g., access of an EMR) to determine whether the at least one event is a potential breach of the electronic patient data. For example, data analyzing component 128 can determine whether an event is a potential breach based on a number of rules/tags that are applied (and/or for which the relevant condition is satisfied), based on determining a weighted score of the rules/tags applied to the event, based on determining certain combinations of rules/tags applied to the event, etc. Moreover, data analyzing component 128 may determine whether an event is a potential breach based on determining patterns in the data and detecting deviations from the patterns, etc., as described herein.

As described, determining the at least one access event at Block 306 may also optionally include, at Block 310, detecting one or more patterns of accessing the electronic patient data by one or more employees based on the plurality of access events. For example, data patterning component 136 may determine the one or more patterns, as described in the rules above, such as typical electronic patient data accessing of the employee (e.g., accessing during certain times, accessing EMRs of patients of certain ages/diagnoses, etc.). In additional examples, data patterning component 136 may pattern typical accesses from EMR access data 122 for one or more employees based on determining viewing of patients in alphabetical order, determining typical patient identifier patterns used in accessing the EMR, determining that the employee usually searches by certain criteria (e.g., name, medical record number (MRN), etc.), determining that the employee normally views old encounters on certain days of the week, month, etc., determining a certain percentage of patients viewed as being male or female, determining a number of patients viewed with similar names, etc. In this regard, as described, data patterning component 136 (and/or rule applying component 134) may determine whether one or more accesses fall outside of a normal distribution or standard deviation of the pattern, and may accordingly determine at least one access (event) as a possible breach.

Method 300 also includes, at Block 312, providing an alert related to the at least one access event based on determining that the at least one access event constitutes possible breach of the electronic patient data. Data presenting component 130 can provide the alert related to the at least one access event based on determining that the at least one access even constitutes possible breach of the electronic patient data, as described. For example, data presenting component 130 can render the alert on an interface (e.g., a dashboard interface of alerts, a patient profile interface graphically depicting EMR access data 122 related to accessing the EMR, etc.), as described further herein. The alert may allow a professional to receive the alert and further investigate the alert to determine whether a possible breach of the electronic patient data has occurred and/or to remediate the possible breach. In an example, the further investigation can be facilitated by indications on interfaces presented by the data presenting component 130 that relate to rules of rule applying component 134, data patterns from data patterning component 136, etc. as described further herein.

FIGS. 4-7 illustrate example interfaces in accordance with aspects described herein with respect to implementation of healthcare provider network platform 102. In some aspects, the interfaces may include graphical user interface (GUI) screens configured to interact with one or more of the various modules/components described herein for providing/receiving information to/from users. This functionality may include substantially any suitable type of application that sends, retrieves, processes, and/or manipulates input data, receives, displays, formats, and/or communicates output data. For example, such interfaces may also be associated with an engine, editor tool, web browser, device application, etc., although other type applications may be utilized. The GUI may include a display having one or more display objects comprising, e.g., configurable icons, buttons, sliders, input boxes, selection options, menus, tabs having multiple configurable dimensions, shapes, colors, text, data and sounds to facilitate operations with the interfaces. In addition, among other things, the GUI may also receive and process user commands from a mouse, touch screen, keyboard, laser pointer, speech input, web site, remote web service and/or other devices such as a camera and/or video content, etc. to affect or modify operations and/or display of the GUI.

Figure 4:

FIG. 4 illustrates an example interface 400 for providing alerts of possible breaches in EMR access data. For example, a compliance officer or other administrative user can log into the healthcare provider network platform 102 (e.g., via another interface), and can be authenticated to access the healthcare provider network platform 102, and in particular interface 400, etc. Interface 400 can include a list of one or more alerts 402 generated for possible breaches in EMR access data. Interface 400 shows the alerts as separated based on a determined priority. In one example, interacting with an alert (e.g., clicking on the alert) may produce another interface for investigating the alert or related information of the associated EMR access event, remediating the possible breach, indicating whether to present similar indications of possible breaches in the future, etc.

FIG. 5 illustrates an example interface 500 for displaying at least a portion of data analysis performed by a healthcare provider network platform. For example, interface 500 displays some clustering of data, which can be performed by a data patterning component 136 as described herein. For example, interface 500 can display a patient summary 502 and employee information 504 related to an access of the patient's EMR as indicated by EMR access data, as described herein. Accesses of the EMR are indicated by dots 506 over a timeline, where each dot 506 corresponds to an access or other action in an EMR of a patient by the listed employee. In addition, interface 500 can depict groupings 508 of employees that are determined to typically access the same EMRs (e.g. within a threshold period of time). For example, one grouping 508 can correlate an orthopedic clinic including a registered nurse, a physician's assistant, and a medical assistant that typically access the same EMRs (e.g., including the depicted EMR for "Frank McDaniel." In this example interface 500, various groupings of employees associated in clinics are shown as accessing the EMR. A registered nurse that is not part of the groupings, however, and/or accessed the EMR outside a threshold time within which other employees in the grouping accessed the EMR, is shown as an alert 510 of possible breach of the data (e.g., based at least on data analyzing component 128 determining that the registered nurse is not part of the groupings). In addition, interacting with the alert 510 can cause display of additional information of the EMR access at 512.

Figure 6:
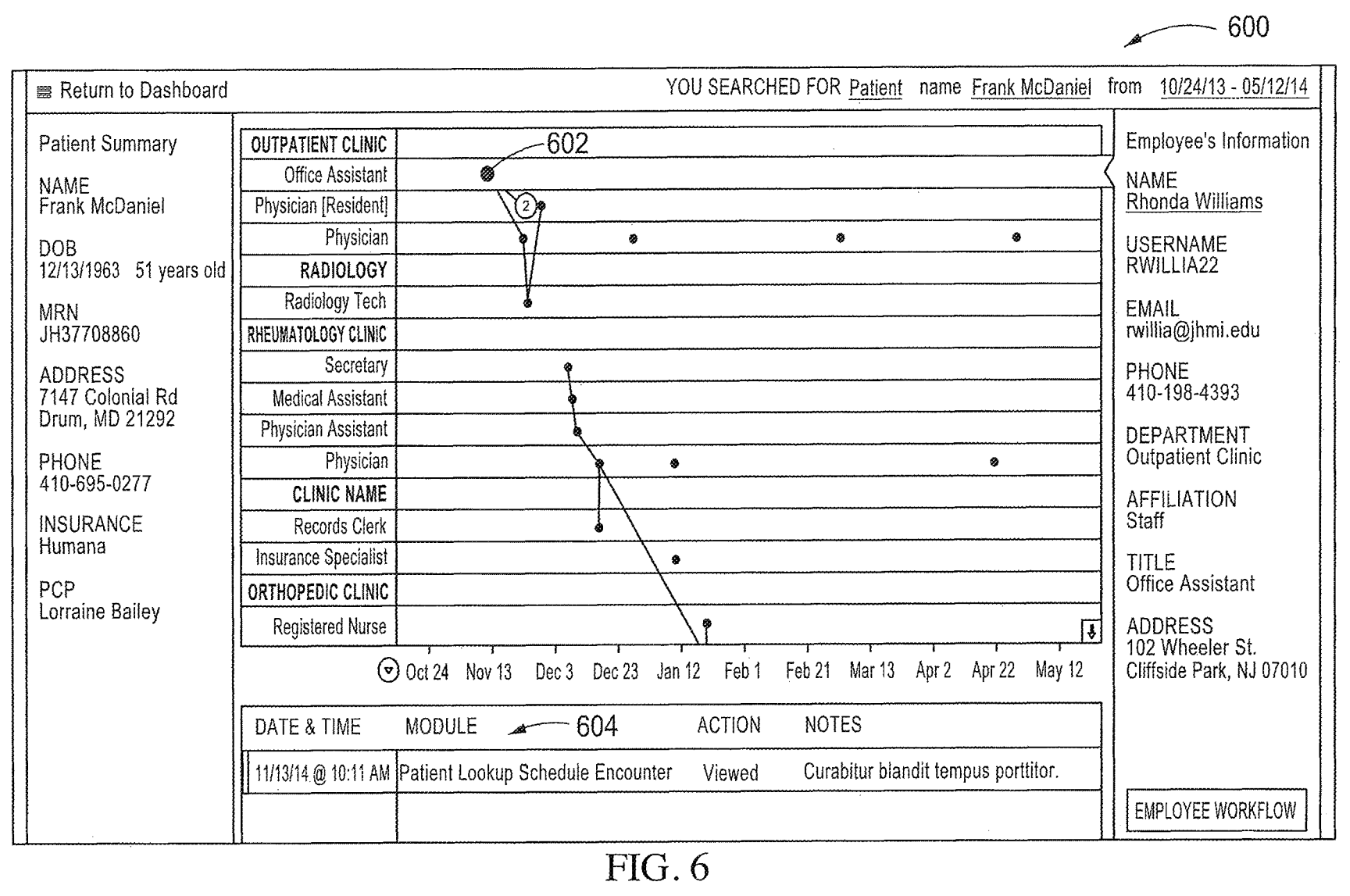

FIG. 6 illustrates an example interface 600 for displaying at least a portion of data analysis performed by a healthcare provider network platform. For example, interface 600 displays some clustering of data, which can be performed by a data patterning component 136 as described herein, and in reference to FIG. 5. In addition, interface 600 can include an access of an EMR by office assistance "Rhonda Williams" at 602. Interacting with the access 602 on the interface 600, though not indicated as an alert, may cause display of additional information regarding the access at 604. Displaying the additional information can allow a compliance officer or other administrator to determine whether a possible breach of the data is actually a breach or not.

FIG. 7 illustrates an example interface 700 for displaying EMR access activity for a given employee 702. For a given access 704 of an EMR, patient information for the EMR can be displayed at 706 along with additional information regarding the access at 708. Employee information 702 may include access information determined by a data analyzing component 128 as described above, such as average access time, number of records viewed per day, time spent in a current EMR, etc., which can facilitate determining whether the employee is possibly breaching the EMR data (e.g., where the time spent in the current EMR is determined to be inconsistent with the average access time).

FIG. 8 illustrates an example of various negative rules/tags 802 for low level alerts that may be applied to electronic patient data, and/or additional negative rules/tags 804 for determining higher level alerts (e.g., by data analyzing component 128). For example, the negative tags 802 for low level alerts may relate to determining an employee checked an EMR for patients with the same full name (e.g., based on EMR data 120 and HR data 124), whether the employee checked an EMR for patients with the same address as theirs, whether the employee checked patients that are employed by the same healthcare provider network (e.g., EMR data 120 indicates employment and/or patient also located in HR data 124), whether an employee checked an EMR for patients with the same last name, whether a pediatrics employee checked an EMR for patients older than 22 (e.g., based on an age/date of birth in the EMR data 120), whether the employee used a workstation they do not typically use, whether the employee accessed an unusual encounter department, whether the employee presented unusual activity for 15 minutes, more generally whether accesses of electronic patient data by a given employee fell outside the normal distribution of behaviors common to employees who are similar in regards to title, department, role, types of patients they encounter, etc., as described above. The EMR access data can be run through one or more of the negative tags 802 (e.g., as one or more rules presented by rule applying component 134 for determining if the negative tags 802 exist in any of the EMR access data 122) to determine whether electronic patient data accesses satisfy one or more of the negative tags 802, and if so, this can indicate a low level alert of possible data breach.

In addition, other negative tags 804 can be applied to the data for which low level alerts are determined to possibly determine higher level alerts. For example, the other negative tags 804 can relate to determining if the employee has no previous history of accessing the patient's EMR, clustering of other employees that have checked the patient's EMR in common with the employee, and/or determining whether the employee and employees are in different clusters (which may indicate collusion among the employees in breaching the EMR data). This may cause generation of a higher level (or priority) alert, as described herein.

In a specific example, given two nurses with the same title, job description, role, department, etc., and the fact that they view the same patient EMRs, or the same type of patient EMRs based on patient diagnoses, conditions, procedures, or demographics, if accesses by one nurse are detected as different from the other (based on a statistical distribution over time, such as increased number of record views per hour, increased time in on patients medical record, access medical records from new workstation, etc.), this behavior may indicate a deviation from the normal, appropriate behavior, and thus a possible breach. Accordingly, data analyzing component 128 may detect such behavior based on statistical analysis of the EMR access data 122 for the two nurses (e.g., by data patterning component 136). For example, data analyzing component 128 may evaluate a plurality of the negative tags 802 for low level alerts to detect a concert of multiple deviations around a single access event, which may increase the suspicious nature of the access.

In another example, a pediatrician may view patient records with an age distribution between 0 years old and 21 years old. The EMR access data 122 can indicate that one pediatrician views an EMR of a 55 year old patient who has never visited that pediatrician's clinic, which is inconsistent with the patient demographic of the pediatrician employee. In addition, to a determination that may relate to detecting the pediatrician accessing an EMR of a 55 year old patient and accessing an EMR of a patient that has not visited the pediatrician's clinic, data analyzing component 128 can perform additional non-rule based determinations as well. For instance, data analyzing component 128 can determine a probability that this patient's medical record is viewed by whomever the last employee to view it followed by this pediatrician to be very low (e.g., below a threshold), which may indicate possible breach of the data. Similarly, data analyzing component 128 can determine the fact that this pediatrician preformed one action in this patient EMR followed by another action to be dissimilar (e.g., outside of a statistical distribution) to the normal sequence of actions this pediatrician takes when he opens a medical record with patients with similar conditions or diagnosis, which can indicate possible breach of the data. In either case, for example, data presenting component 130 may present an indication of the possible breach on an interface for viewing by a device (e.g., device 106) to analyze, investigate, and/or remediate the possible breach (e.g., based on other data around the access as determined by data analyzing component 128, stored by EMR data 120, EMR access data 122, HR data 124, etc., and/or the like).

In another specific example, an insurance/billing specialist accesses patient EMRs at similar rates of progression (e.g., accesses new record on average of every 50 seconds). Inside every EMR, the billing specialist may view new procedures accesses that patient's insurance information. While this behavior is not perfectly repetitive, it can follow a normal distribution of likely sequences of events. If this pattern is disturbed beyond a normal distribution to view a medical record of a patient who is also a fellow employee, this may indicate a possible breach, and data analyzing component 128 may accordingly detect this disturbing of the pattern beyond a determined normal distribution in EMR access data 122 as a possible breach. For example, it can be determined that the billing specialist does not view insurance information (which is consistent with the sequence of events typically performed by the billing specialist), but instead views lab results (which is not consistent with sequence of events typically performed by the billing specialist), which may indicate possible breach. It is to be appreciated that the deviation in behavior can be detected by automatically observing baseline normalities (e.g., by a data patterning component 136) and associating the normalities to a curve based on multiple dimensions (title, department, location, date of hire, etc.). Data analyzing component 128 can then use the normalities to detect deviation and possible breach (e.g., by a data analyzing component 128), which may be based on a determined degree of deviation.

FIG. 9 illustrates an example method 900 for processing drug dispensing data to determine possible misappropriation of drugs. Method 900 includes, at Block 902, receiving data related to a plurality of dispensing events of an electronic drug dispensing system by one or more employees. Data receiving component 126 can receive data related to the plurality of dispensing events of the electronic drug dispensing system by one or more employees. This can optionally include, at Block 904, receiving data from dispensing logs, EMRs, and/or human resources data. Thus, for example, data receiving component 126 can receive data as drug dispensing data 152 of the electronic drug dispensing system 150, EMRs (e.g., EMR data 120, which may include prescriptions or other information associated with drugs dispensed or to be dispensed), human resources data (e.g., HR data 124, which may include employee-related data), and/or the like. As described, data receiving component 126 may receive this data from one or more data sources including one or more electronic drug dispensing systems 150 or a host system to which multiple electronic drug dispensing systems 150 connect, a healthcare provider network and/or other system or network, etc., which may be distributed across one or more networks, co-located, and/or the like.

Method 900 also includes, at Block 906, determining at least one dispensing event of the plurality of dispensing events by the one or more employees that constitute possible misappropriation of drugs. Data analyzing component 128 can determine the plurality of dispensing events by the one or more employees that constitute possible misappropriation of drugs. For example, the plurality of dispensing events may include events of actual dispensing requests and/or fulfillment of such requests by the electronic drug dispensing system 150, created wasting events where drugs dispensed based on a request are wasted, and/or other interactions with the electronic drug dispensing system 150 by healthcare professionals.

In an example, determining the at least one dispensing event at Block 906 can optionally include, at Block 908, detecting the at least one dispensing event based on one or more rules. Data analyzing component 128 may include rule applying component 134 for detecting the at least one dispensing event based on the one or more rules. In one example, rule applying component 134 can apply one or more rules to the data using a rules-based mechanism to determine the at least one dispensing event constituting the possible misappropriation of drugs. For instance, the one or more rules may relate to detecting dispensing or wasting of a certain drug over a threshold amount over a period of time, by a single healthcare professional, by healthcare professionals in the same department or on the same floor (e.g., of a hospital), etc. In one specific example, all dispensing of a certain drug type (e.g., pain killers) over a threshold quantity (per period of time, per dispensing, etc.) may be detected as a possible misappropriation. In any case, in this example, data analyzing component 128 may determine a possible misappropriation of drugs where one or more rules are satisfied, an indication of which may be presented to an interface as described herein for further investigation.

In another example, the one or more rules may relate to determining whether data relating to a position of the employee from HR data 124 (e.g., or inferred through other data, such as determining a synthetic department of the employee as described further below) corresponds to the type of drugs and/or quantity of the drugs being dispensed for the patient. For instance, where different drugs are dispensed (if possible from the electronic drug dispensing system 150) or a higher quantity is dispensed, this may indicate possible misappropriation of drugs. For example, one or more such rules may be based on a position and/or department (e.g., rules may be present for physician assistants, nurses, techs, etc., but perhaps not for doctors, and/or may relate to whether the type of drug being dispensed corresponds to a department of the employee based on HR data 124). In an example, rule applying component 134 may apply multiple rules in detecting a possible misappropriation of drugs (e.g., similar last name between employee and patient along with the type or quantity of drug dispensed).

It is to be appreciated that rule applying component 134 may apply the one or more rules to filter the data for possible misappropriations, and the possible misappropriations may further be analyzed based on patterning, as described below, and/or the data may be analyzed based instead on patterning without applying the one or more rules described above. In another example, the one or more rules may relate to the patterned data, and thus rule applying component 134 may apply one or more rules to patterned data determined by data patterning component 136 to detect possible misappropriations of drugs.

In any case, determining the at least one dispensing event that constitute possible misappropriation of drugs may additionally or alternatively optionally include, at Block 910, detecting one or more patterns of dispensing drugs by one or more employees based on the plurality of dispensing events. Data analyzing component 128 may include data patterning component 136 for detecting one or more patterns of dispensing the drugs by one or more employees based on the plurality of dispensing events. For example, data patterning component 136 may detect the one or more patterns at least in part by clustering the data related to dispensing (or wasting) of drugs based on detecting commonalities in the data, machine-learning commonalities in the data, network analyzing commonalities in the data (e.g., generating Markov chains), etc. The commonalities can be determined based on computing statistical inferences such that data commonalities are meaningful. For instance, data patterning component 136 may detect patterns by a given employee (e.g., typical drug dispensing times by the employee), patterns for groups of employees (e.g., determining that a group of employees typically dispense similar drugs as part of treating patients with similar condition), etc. In an example, in this regard, data analyzing component 128 may determine the at least one dispensing event as a pattern of dispensing events that may constitute possible misappropriation. In another example, data analyzing component 128 ma determine the at least one dispensing that constitutes possible misappropriation of drugs based at least in part on detecting that the at least one dispensing is inconsistent with, or an outlier of, the one or more patterns determined by the data patterning component 136.

In one specific example, data patterning component 136 may detect a pattern of dispensing events that may be indicative of misappropriation, such as wasting of similar drugs over a period of time, wasting of drugs for the same patient or patients with similar diagnoses or prescriptions over a period of time, etc. Moreover, in an example, data patterning component 136 may detect the pattern for a single healthcare professional dispensing the drugs, professionals that are on the same team or same department, professionals that are treating the same or similar patients, professionals that are working similar shifts when dispensing/wasting occurs, and/or the like.

In another specific example, data patterning component 136 may detect that dispensing by the employee typically occur at a given dispenser in the healthcare provider network (e.g., based on an identifier, network address, etc. related to the dispenser), and data analyzing component 128 may determine whether the drug dispensing data 152 includes one or more dispensings by the employees from a different dispenser, which may indicate a possible misappropriation (e.g., based additionally on the drug type, amount, and/or the like).

It is to be appreciated that data patterning component 136 can constantly or periodically generate the one or more patterns such that the patterns can evolve over time based on changes to other data in the healthcare provider network platform 102 (e.g., addition, movement, removal, etc. of employees in the drug dispensing data 152 and/or HR data 124, etc.). Moreover, for example, drug dispensing data 152 can be periodically received in data logs, received using a request/receive mechanism (e.g., file transfer protocol (FTP)), publish/subscribe mechanism, etc.).

Method 900 also includes, at Block 912, providing an alert related to the at least one access event based on determining that the at least one access event constitutes possible breach of the electronic patient data. Data presenting component 130 can provide the alert related to the at least one access event based on determining that the at least one access even constitutes possible breach of the electronic patient data. For example, data presenting component 130 can render the alert on an interface (e.g., a dashboard interface of alerts, a patient profile interface graphically depicting EMR access data 122 related to accessing the EMR, etc.), as described further herein. The alert may allow a professional to receive the alert and further investigate the alert to determine whether a possible breach of the data has occurred and/or to remediate the possible breach. In an example, the further investigation can be facilitated by indications on interfaces presented by the data presenting component 130 that relate to rules of rule applying component 134, data patterns from data patterning component 136, etc. as described further herein.

In addition, in an example, data analyzing component 128 may determine a confidence level or priority related to a detected possible misappropriation, which may be based on which of the one or more rules the detected possible misappropriation satisfies, which of the one or more patterns to which the detected possible misappropriation relates, a level of deviation from the one or more patterns, and/or the like. In this example, data presenting component 130 may provide a representation of the dispensing (or wasting) event along with any confidence or priority information. Specific examples of interfaces for providing the alerts and/or allowing further investigation are shown herein. For example, the alert may also identify the healthcare professional dispensing the drug, the type and/or amount or drug, a wasting event, prescription information, other dispensing events by the healthcare professional or other healthcare professionals that may be related to the possible misappropriation, etc.

Method 900 may optionally include, at Block 914, employing feedback received related to determining the at least one dispensing event constitutes possible misappropriation of drugs in determining whether one or more subsequent dispensing events constitute possible misappropriation of drugs. For example, feedback component 132 can receive and employ feedback related to determining the at least one dispensing event constitutes possible misappropriation of drugs in determining whether one or more subsequent dispensing events constitute possible misappropriation of drugs. In an example, feedback can be provided via one or more interfaces to indicate whether a possible misappropriation detection is actually considered a misappropriation, whether misappropriation detection is too conservative, and/or whether more conservative misappropriation detection is desired. Data analyzing component 128 can utilize the feedback information to automatically activate/deactivate one or more rules used by rule applying component 134, one or more patterns detected in the drug dispensing data 152 by data patterning component 136, one or more numbers of standard deviations for detecting possible misappropriation, etc. to achieve a desired level of consideration for determining whether dispensings defined in the drug dispensing data 152 indicate possible misappropriation of drugs.

FIGS. 10-14 illustrate example interfaces in accordance with aspects described herein with respect to implementation of healthcare provider network platform 102. In some aspects, the interfaces may include graphical user interface (GUI) screens configured to interact with one or more of the various modules/components described herein for providing/receiving information to/from users. This functionality may include substantially any suitable type of application that sends, retrieves, processes, and/or manipulates input data, receives, displays, formats, and/or communicates output data. For example, such interfaces may also be associated with an engine, editor tool, web browser, device application, etc., although other type applications may be utilized.

The GUI may include a display having one or more display objects comprising, e.g., configurable icons, buttons, sliders, input boxes, selection options, menus, tabs having multiple configurable dimensions, shapes, colors, text, data and sounds to facilitate operations with the interfaces. In addition, among other things, the GUI may also receive and process user commands from a mouse, touch screen, keyboard, laser pointer, speech input, web site, remote web service and/or other devices such as a camera and/or video content, etc. to affect or modify operations and/or display of the GUI.

Figure 10:
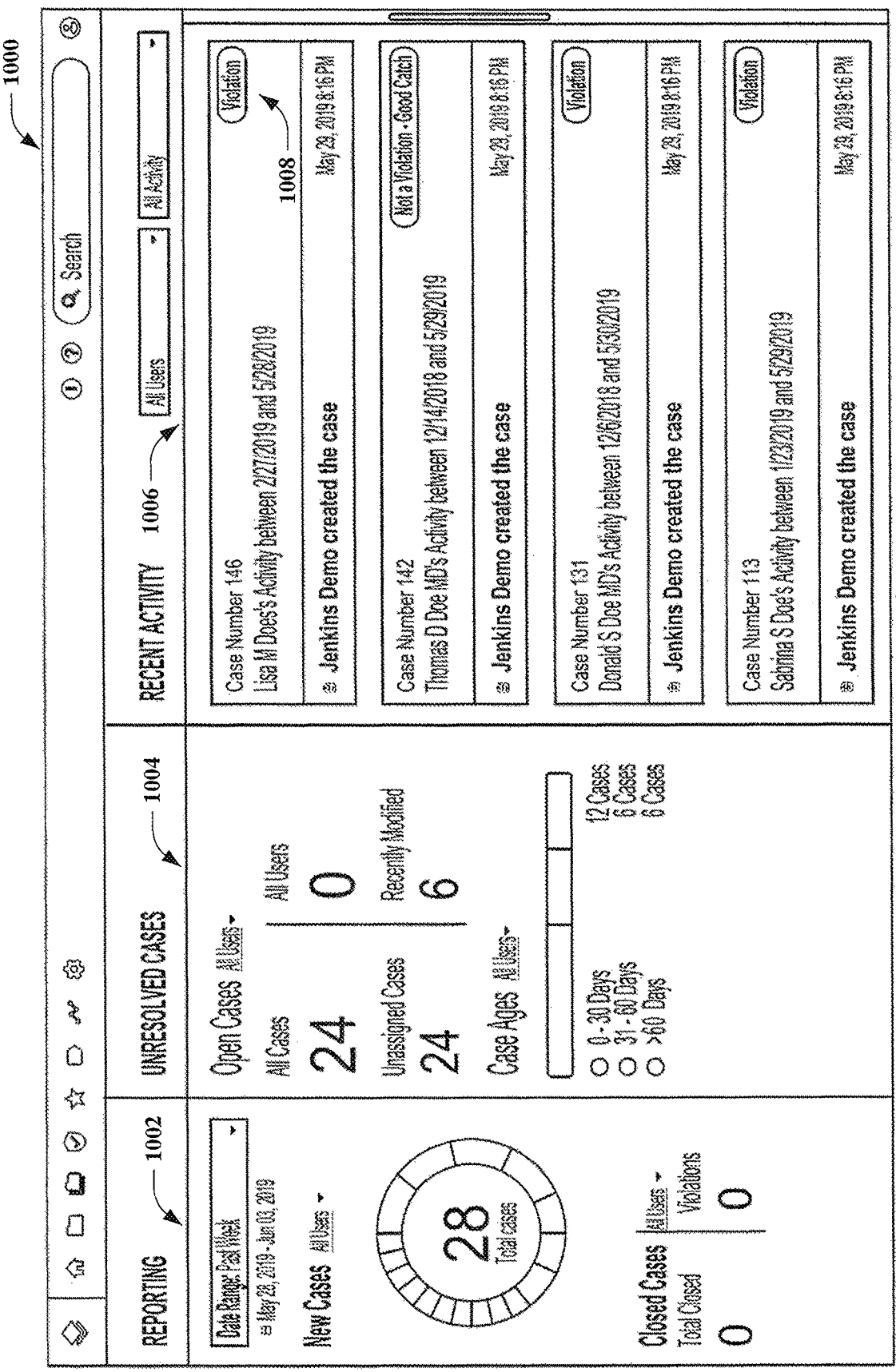

FIG. 10 illustrates an example interface 1000 for providing alerts of possible misappropriation of drugs (e.g., as detected from drug dispensing data 152). For example, a compliance officer or other administrative user can log into the healthcare provider network platform 102 (e.g., via another interface), and can be authenticated to access the healthcare provider network platform 102, and in particular interface 1000, etc. Interface 1000 can include a summary 1002 of cases generated (e.g., by the data presenting component 130) as possible misappropriations of drugs, and another summary 1004 indicating a number of cases unassigned to administrative personnel, recently modified cases, case age, etc. In addition, interface 1000 can include a listing 1006 of recent activity of cases that are identified as possible misappropriations of drugs. In one example, each case may include a feedback indicator 1008 to allow for indicating (e.g., as feedback) whether the identification is indeed a violation (e.g., a valid misappropriation) or not a violation (e.g., a false positive).

Figure 11:
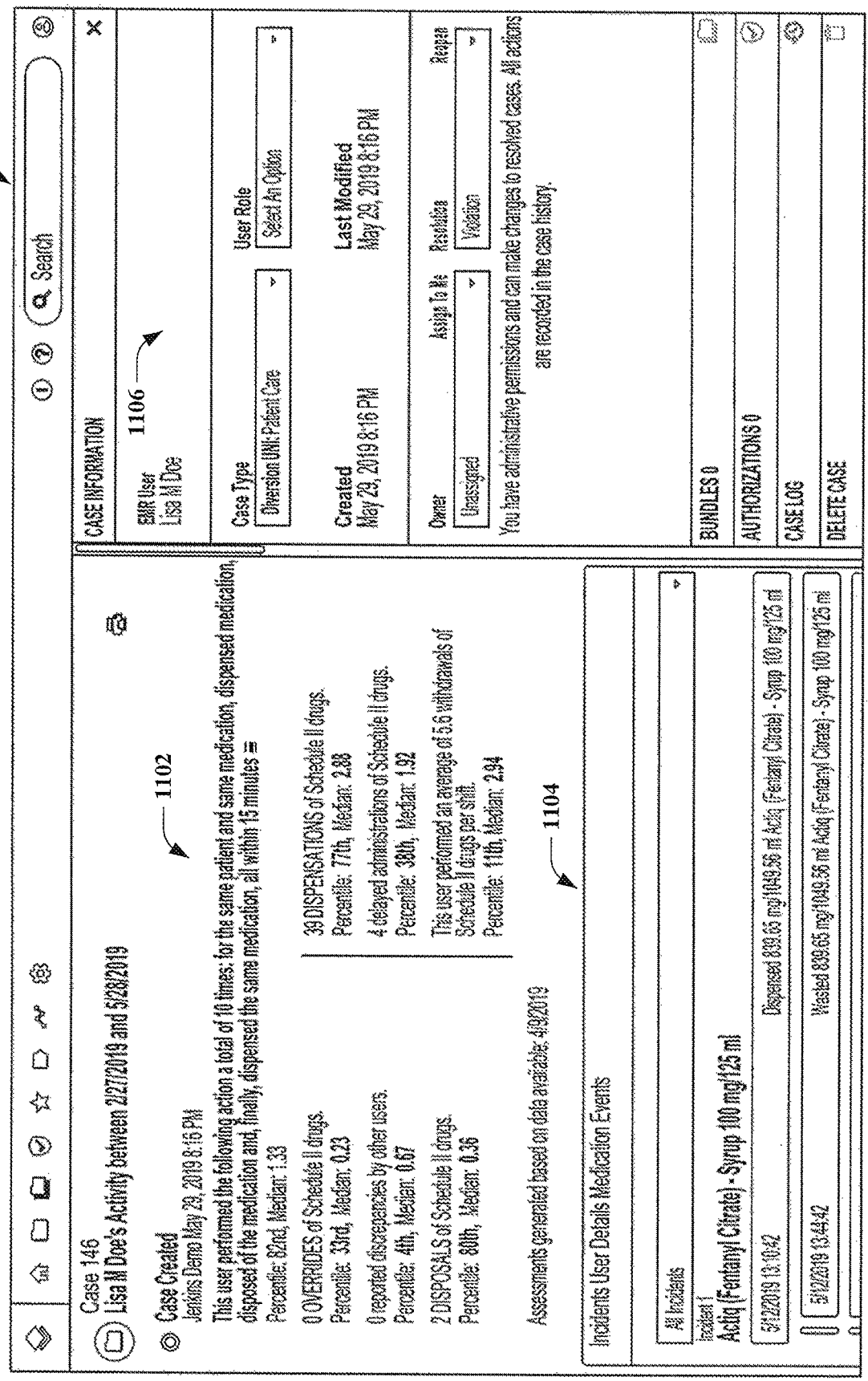

FIG. 11 illustrates an example interface 1100 for displaying at least a portion of data analysis performed by a healthcare provider network platform. In an example, interface 1100 can be displayed when selecting a case from interface 1000. For example, interface 1100 displays a listing 1102 of dispensing event data, which may be determined to be possible misappropriation of drugs for a healthcare professional or otherwise considered in making such a determination. The listing 1102 can include a specific association of data determined to be possible misappropriation (e.g., the user performing the action a total of 10 times in 15 minutes), along with more general information about the user's usage of the electronic drug dispensing system 150 determined by data analyzing component 128 from the drug dispensing data 152. In addition, for example, the more general information can include statistical information regarding the user's usage and peer usage, etc., which may be used to identify the user as an outlier of their peers (and thus suspect of misappropriating drugs). In this example, the interface 1100 can display a listing of incidents 1104 determined for the healthcare professional to allow for performing investigation of the healthcare professional for possible misappropriation of drugs. For example, the listing of incidents 1104 may be of incidents detected from the drug dispensing data 152 that resulted in determining the possible misappropriation of drugs. Interface 1100 can also include case information 1106 displaying information for updating case-specific data, such as a case type, healthcare professional role, etc.

Figure 12:
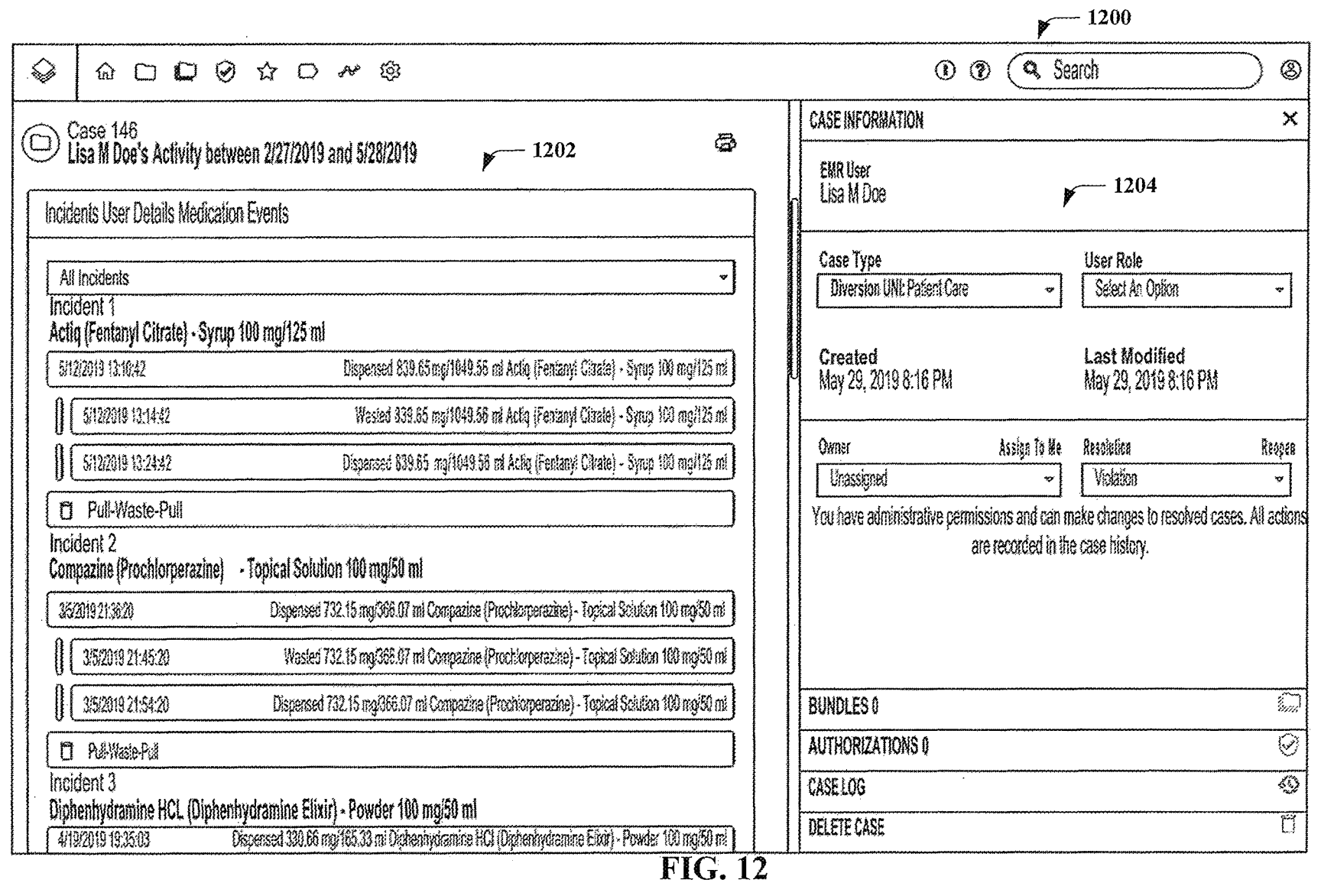

FIG. 12 illustrates an example interface 1200 for displaying at least another portion of data analysis performed by a healthcare provider network platform. In an example, interface 1200 can be displayed when selecting a case from interface 1000 or selecting incidents to view from interface 1100. For example, interface 1200 displays a listing 1202 of incidents for the healthcare professional suspected of misappropriating drugs, which may be determined to be possible misappropriation of drugs for a healthcare professional or otherwise considered in making such a determination. The listing 1202 can include listings of detected incidents and related drug dispensing records for investigation. In addition, interface 1200 can include case information 1204 displaying information for updating case-specific data, such as a case type, healthcare professional role, etc.

Figure 13:
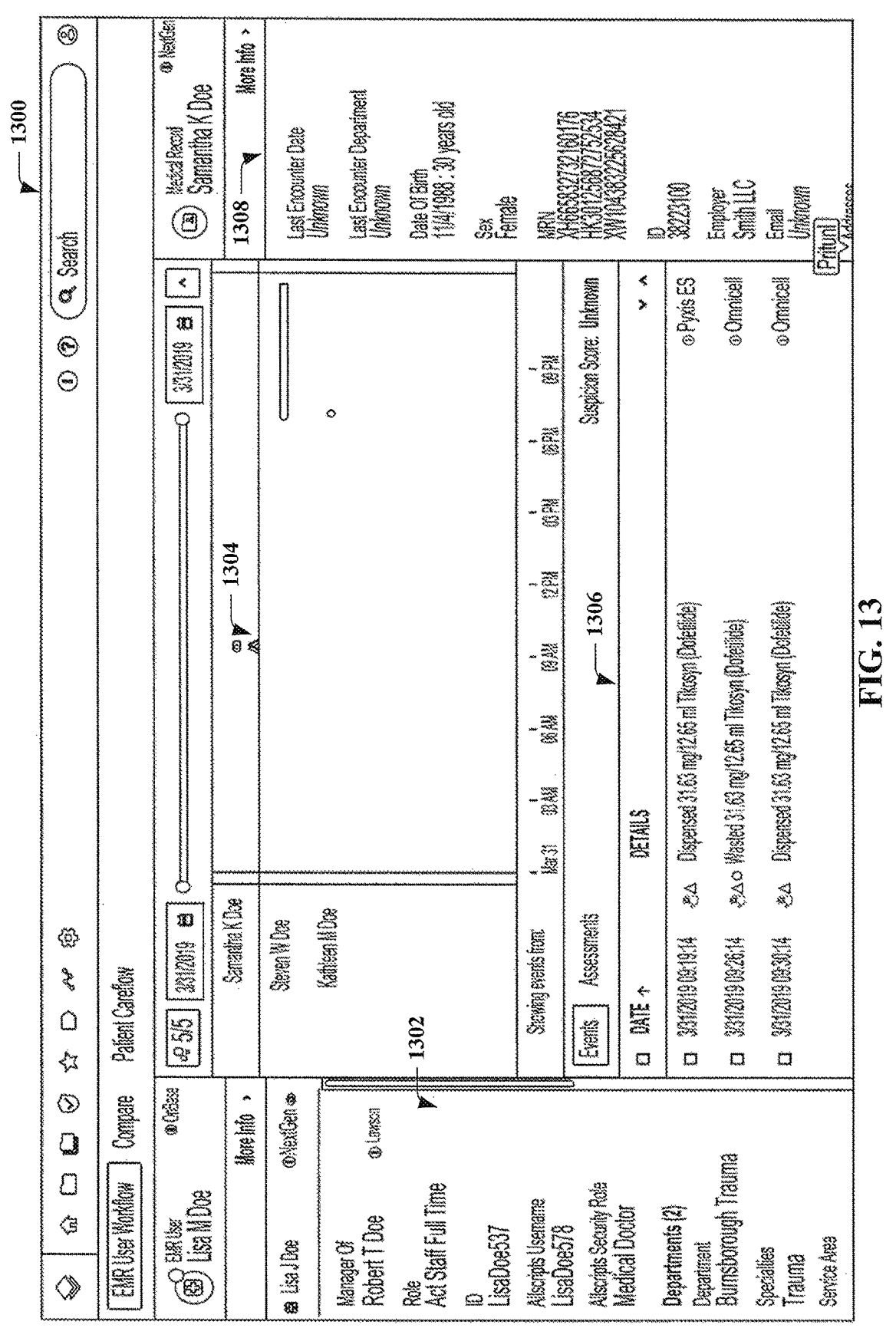

FIG. 13 illustrates an example interface 1300 for displaying at least another portion of data analysis performed by a healthcare provider network platform. In an example, interface 1300 can be displayed when selecting an incident from interface 1100 or 1200. For example, interface 1300 displays information 1302 of the healthcare professional suspected of misappropriating drugs. Interface 1300 also displays a timeline 1304 of accessing the electronic drug dispensing system 150 for dispensing drugs for a given patient, along with a triangular icon to indicate the dispensings or wastings that are part of the detected incident. A listing 1306 of the dispensing or wasting events is also displayed on the interface 1300. In addition, for a selected patient, corresponding EMR data 1308 can be displayed.

Figure 14:
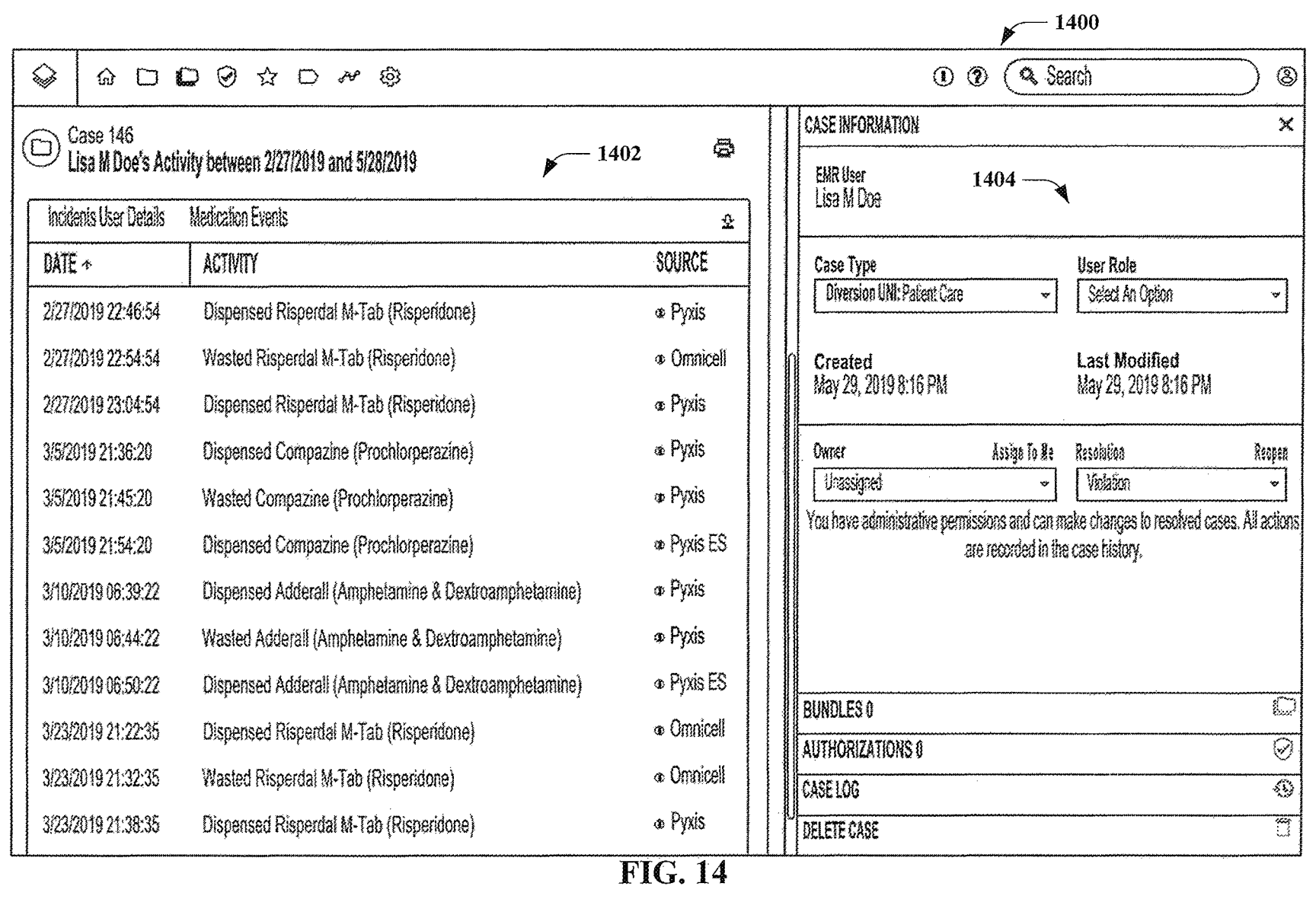

FIG. 14 illustrates an example interface 1400 for displaying at least another portion of data analysis performed by a healthcare provider network platform. In an example, interface 1400 can be displayed when selecting to display medication events from interface 1100. For example, interface 1400 displays a listing 1402 of medication events performed by the healthcare professional suspected of misappropriating drugs. In addition, interface 1400 can include case information 1404 displaying information for updating case-specific data, such as a case type, healthcare professional role, etc.

Figure 15:
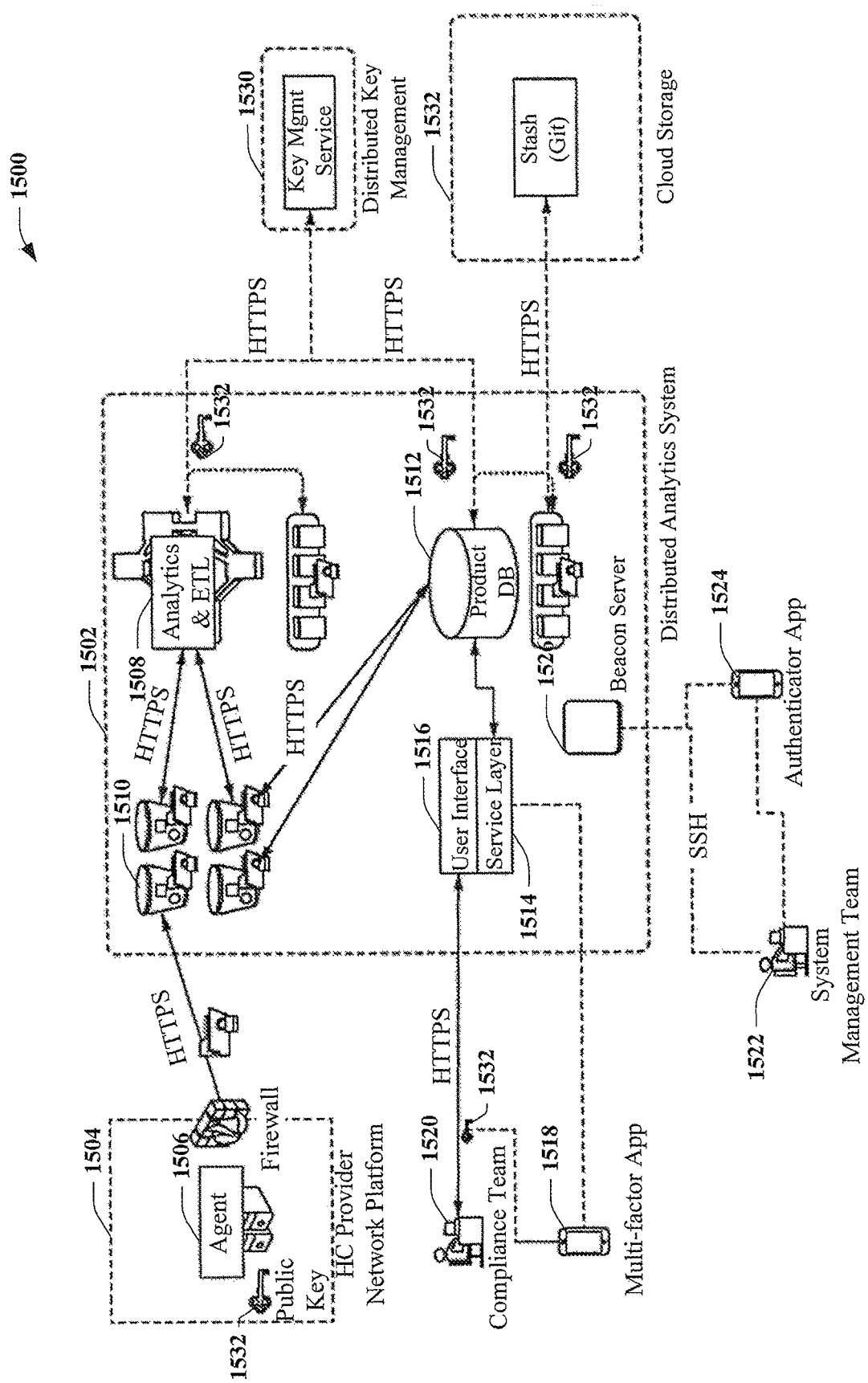
FIG. 15 is an example system architecture in accordance with aspects described herein.

FIG. 15 illustrates an example system 1500 in accordance with aspects described herein. For example, system 1500 may include various distributed components as described in reference to the previous figures. System 1500 may include, for example, a distributed analytics system 1502, which may perform one or more functions of the components described herein (e.g., data receiving component 126, data analyzing component 128, data presenting component 130, etc.). For example, distributed analytics system 1502 may receive data from a healthcare (HC) provider network platform 1504 (which may be similar to HC provider network platform 102 but having the various components distributed to distributed analytics system 1502). For example, HC provider network platform 1504 may include an agent 1506 that can operate without the HC provider network platform 1504 for transferring data from one or more repositories in the HC provider network platform 1504 (e.g., EMR data, EMR access data, HR data, drug dispensing data, etc., as described) to distributed analytics system 1502 for subsequent analysis. For example, agent 1506 may transfer the data to distributed analytics system 1502 via secured hypertext transfer protocol (HTTPS) through one or more firewalls.

In an example, distributed analytics system 1502 can include an analytics and extract, transform, and load (ETL) component 1508 (which may be similar to and/or include at least a portion of data analyzing component 128) that receives data from one or more filter components 1510 (which may also be similar to and/or include at least a portion of data analyzing component 128). For example, the filter components 1510 may apply whitelist filters, as described, to filter out EMR access data that may be indicative of acceptable accesses of electronic patient data (e.g., legitimate authorized accesses, as described above), and the remaining EMR access data may be provided to the analytics and ETL component 1508 for further analysis. In an example, distributed analytics system 1502 may also include a product database 1512 that may store data received from the one or more filter components 1510, analytics and ETL component 1508, etc., which may include data regarding possible breaches or misappropriation of drugs, general EMR access data, etc., for alerting, viewing, etc. via a service layer 1514 and/or associated user interface 1516.

For example, where analytics and ETL component 1508 detects a possible breach or misappropriation of drugs, as described above, the related information may be communicated to the product database 1512 and then to service layer 1514 to alert an application (e.g., multi-factor application 1518) of the possible breach or misappropriation of drugs. Based on this alert, or otherwise, a compliance team 1520 (e.g., using one or more devices) may access distributed analytics system 1502 via user interface 1516 over HTTPS to view the possible breach and/or substantially any EMR access data (e.g., as shown in GUIs 400, 500, 600, 700, 1000, 1100, 1200, 1300, 1400, and/or similar interfaces as described herein). User interface 1516 may display the data based on accessing product database 1512 via service layer 1514 to obtain the data for display (e.g., based on one or more queries to the product database 1512). In another example, a system management team 1522 (e.g., using one or more devices) may access the distributed analytics system 1502 (e.g., via an authenticator application 1524 and beacon server 1526 architecture) to modify one or more components or related data (e.g., rules, tags, metadata, etc.) of the distributed analytics system 1502.

Additionally, for example, system 1500 may include a distributed key management component 1530 for managing one or more security keys used in accessing data from distributed analytics system 1502. For example, the keys can include one or more private keys, public keys, private/public key pairs, etc. used to authenticate requests for data from distributed analytics system 1502. Additionally, in an example, cloud storage 1532 can be provided for at least a portion of the data in product database 1512.

Figure 16:
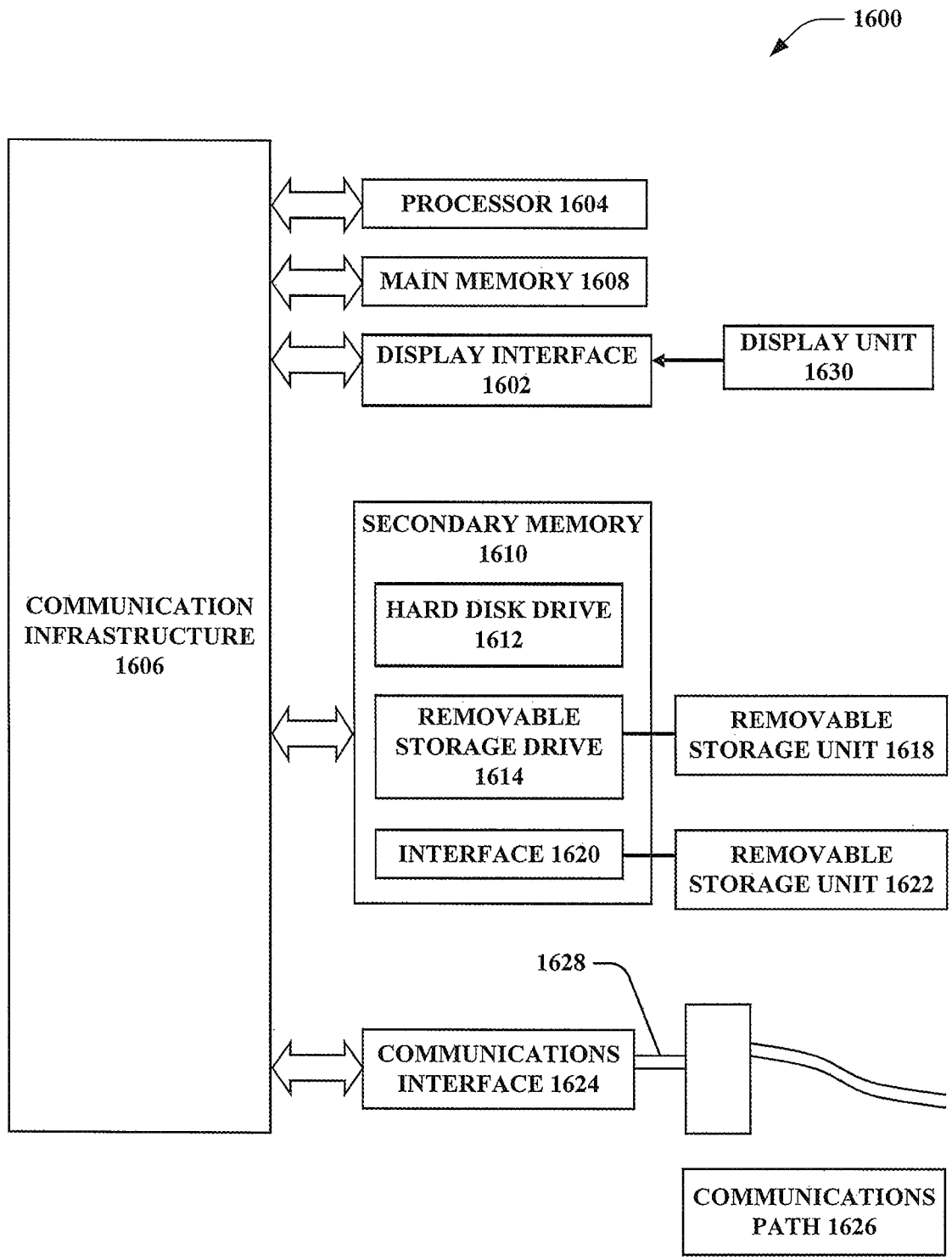
FIG. 16 is an example system diagram of various hardware components and other features, for use in accordance with aspects described herein.

In some variations, aspects described herein may be directed toward one or more computer systems capable of carrying out the functionality described herein. An example of such a computer system 1600 is shown in FIG. 16.

Computer system 1600 may include one or more processors, such as processor 1604. The processor 1604 is connected to a communication infrastructure 1606 (e.g., a communications bus, cross-over bar, or network). Various software aspects are described in terms of this example computer system. After reading this description, it will become apparent to a person skilled in the relevant art(s) how to implement the described subject matter using other computer systems and/or architectures. For example, processor 1604 can implement the components 126, 128, 130, 132, 134, 136, etc. described in connection with a healthcare provider network platform 102 (FIG. 1), related methods 200, 300, 900 and/or Blocks thereof (FIGS. 2, 3, 9), etc.

Computer system 1600 may include a display interface 1602 that forwards graphics, text, and other data from the communication infrastructure 1606 (or from a frame buffer not shown) for display on a display unit 1630. Computer system 1600 also includes a main memory 1608, preferably random access memory (RAM), and may also include a secondary memory 1610. The secondary memory 1610 may include, for example, a hard disk drive 1612 and/or a removable storage drive 1614, representing a floppy disk drive, a magnetic tape drive, an optical disk drive, a flash memory drive, etc. The removable storage drive 1614 reads from and/or writes to a removable storage unit 1618 in a well-known manner. Removable storage unit 1618, represents a floppy disk, magnetic tape, optical disk, flash memory card, etc., which is read by and written to removable storage drive 1614. As will be appreciated, the removable storage unit 1618 includes a computer usable storage medium having stored therein computer software and/or data.

In alternative aspects, secondary memory 1610 may include other similar devices for allowing computer programs or other instructions to be loaded into computer system 1600. Such devices may include, for example, a removable storage unit 1622 and an interface 1620. Examples of such may include a program cartridge and cartridge interface (such as that found in video game devices), a removable memory chip (such as an erasable programmable read only memory (EPROM), or programmable read only memory (PROM)) and associated socket, and other removable storage units 1622 and interfaces 1620, which allow software and data to be transferred from the removable storage unit 1622 to computer system 1600.

Computer system 1600 may also include a communications interface 1624. Communications interface 1624 allows software and data to be transferred between computer system 1600 and external devices. Examples of communications interface 1624 may include a modem, a network interface (such as an Ethernet card), a communications port, a Personal Computer Memory Card International Association (PCMCIA) slot and card, etc. Software and data transferred via communications interface 1624 are in the form of signals 1628, which may be electronic, electromagnetic, optical or other signals capable of being received by communications interface 1624. These signals 1628 are provided to communications interface 1624 via a communications path (e.g., channel) 1626. This path 1626 carries signals 1628 and may be implemented using wire or cable, fiber optics, a telephone line, a cellular link, a radio frequency (RF) link and/or other communications channels. In this document, the terms "computer program medium" and "computer usable medium" are used to refer generally to media such as a removable storage drive 1614, a hard disk installed in hard disk drive 1612, and signals 1628. These computer program products provide software to the computer system 1600. Aspects of the described subject matter may be directed to such computer program products.

Computer programs (also referred to as computer control logic) are stored in main memory 1608 and/or secondary memory 1610. Computer programs may also be received via communications interface 1624. Such computer programs, when executed, enable the computer system 1600 to perform the features of the subject matter described herein. In particular, the computer programs, when executed, enable the processor 1604 to perform the features of the described subject matter. Accordingly, such computer programs represent controllers of the computer system 1600.

In an aspect where the aspects described herein are implemented using software, the software may be stored in a computer program product and loaded into computer system 1600 using removable storage drive 1614, hard disk drive 1612, or interface 1620. The control logic (software), when executed by the processor 1604, causes the processor 1604 to perform the functions of the subject matter described herein. In another aspect, the subject matter described herein may be implemented primarily in hardware using, for example, hardware components, such as application specific integrated circuits (ASICs). Implementation of the hardware state machine so as to perform the functions described herein will be apparent to persons skilled in the relevant art(s). In yet another aspect, variations of the described subject matter may be implemented using a combination of both hardware and software.

In one example, display interface 1602 may provide interfaces related to the healthcare provider network platform 102 (e.g., provided by data presenting component 130, etc.) or related GUIs 400, 500, 600, 700, 1000, 1100, 1200, 1300, 1400, and/or similar interfaces as described herein. Interaction with these interfaces may be provided via input devices connected to communication infrastructure 1606, such as a keyboard, mouse, touch screen, voice input, and/or the like.

Figure 17:
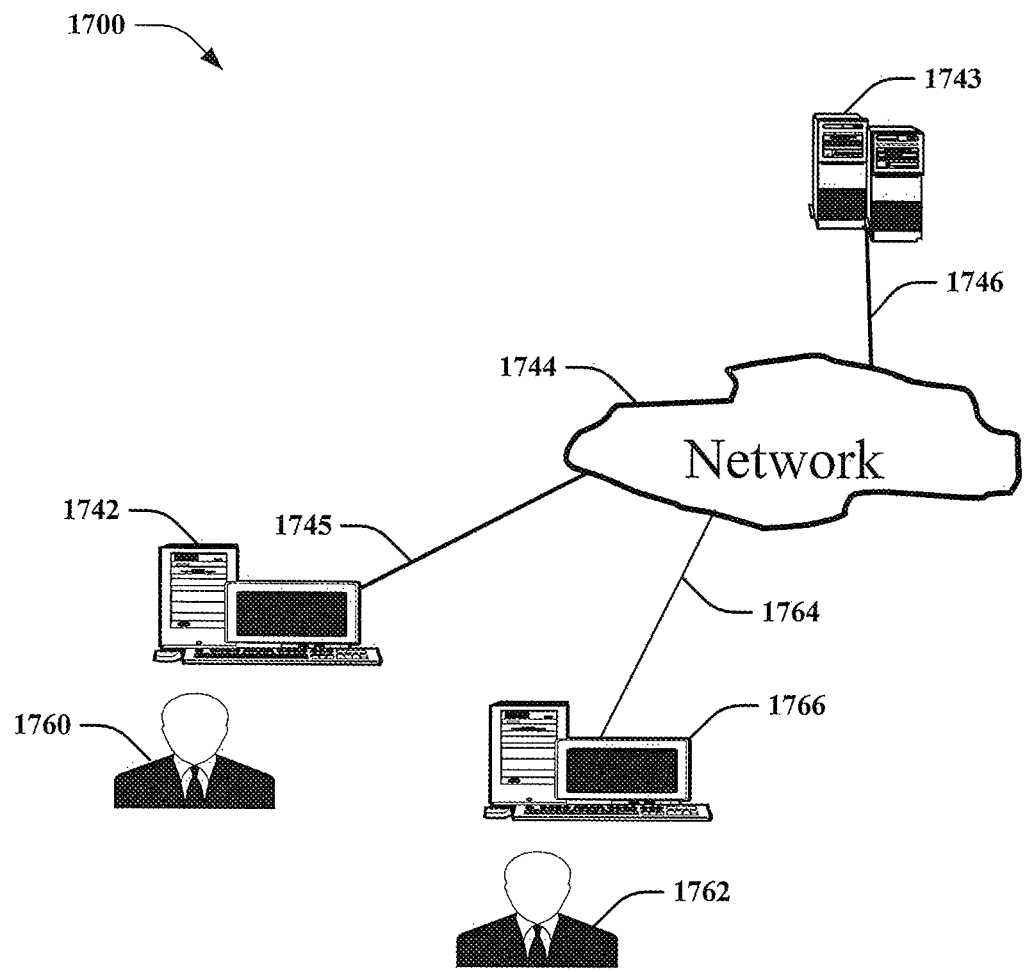
FIG. 17 is a block diagram of various example system components, for use in accordance with aspects described herein.

FIG. 17 shows a communication system 1700 involving use of various features in accordance with aspects described herein. The communication system 1700 may include one or more assessors 1760, 1762 (also referred to interchangeably herein as one or more "users", "entities," etc.) and one or more terminals 1742, 1766 accessible by the one or more assessors 1760, 1762. In one aspect, operations in accordance with aspects described herein may include, for example, input and/or accessed by an accessor 1760 via terminal 1742, such as personal computers (PCs), minicomputers, mainframe computers, microcomputers, telephonic devices, or wireless devices, such as personal digital assistants ("PDAs") or a hand-held wireless devices coupled to a remote device 1743, such as a server, PC, minicomputer, mainframe computer, microcomputer, or other device having a processor and a repository for data and/or connection to a repository for data, via, for example, a network 1744, such as the Internet or an intranet, and couplings 1745, 1764. The couplings 1745, 1764 include, for example, wired, wireless, or fiberoptic links. In another aspect, the methods and systems described herein may operate in a stand-alone environment, such as on a single terminal.

While the foregoing has been described in conjunction with the example aspects outlined above and further described in the figures, various alternatives, modifications, variations, improvements, and/or substantial equivalents, whether known or that are or may be presently unforeseen, may become apparent to those having at least ordinary skill in the art. Accordingly, the exemplary aspects, as set forth above, are intended to be illustrative, not limiting. Various changes may be made without departing from the spirit and scope of the subject matter described herein. Therefore, aspects described herein intended to embrace all known or later-developed alternatives, modifications, variations, improvements, and/or substantial equivalents.

What is claimed is:

1. A computer-implemented method for processing drug dispensing data to determine a possible drug misappropriation, the method comprising:
receiving, by a distributed analytics system, drug dispensing data from one or more data sources, the one or more data sources comprising at least one of: one or more dispensing logs or one or more electronic medical records (EMRs) received from a healthcare provider network;
identifying, by the distributed analytics system, a plurality of dispensing events by a plurality of users based at least in part on the one or more dispensing logs;
detecting, by the distributed analytics system, at least one drug misappropriation event corresponding to at least one of the plurality of dispensing events based on at least one of one or more rules or one or more drug dispensing patterns;

determining, by the distributed analytics system, at least one confidence level corresponding to the at least one detected possible drug misappropriation, wherein the at least one confidence level is based on at least one of which of the one or more rules the at least one detected possible drug misappropriation satisfies, which of the one or more drug dispensing patterns to which the at least one detected possible drug misappropriation relates, or a level of deviation of the at least one detected possible drug misappropriation from the one or more drug dispensing patterns; and causing to display on an interface of a user device, by the distributed analytics system, an alert that includes:

detected possible drug misappropriation information of the at least one detected possible drug misappropriation and the at least one confidence level, and a feedback component for receiving feedback that enables activation or deactivation of a rule of the one or more rules or a pattern of the one or more drug dispensing patterns.

2. The computer-implemented method of claim 1, wherein the alert identifies a user of the plurality of users that dispensed the drug, a drug type, an drug amount, a wasting event, or prescription information.

3. The computer-implemented method of claim 1, the method further comprising:

receiving, by the distributed analytics system and via the feedback component, feedback indicating whether the at least one detected possible drug misappropriation is an actual drug misappropriation.

4. The computer-implemented method of claim 3, wherein the feedback received via the feedback component activates or deactivates a rule of the one or more rules or a pattern of the one or more drug dispensing patterns.

5. The computer-implemented method of claim 4, wherein the feedback is received from a user using one or more graphical elements displayed on a graphical user interface.

6. The computer-implemented method of claim 1, wherein detecting, by the distributed analytics system, the at least one drug misappropriation event corresponding to at least one of the plurality of dispensing events further includes:

determining, by the distributed analytics system, that the at least one of the plurality of dispensing events falls outside of a standard deviation of the one or more drug dispensing patterns; and based on the determining, indicating, by the distributed analytics system, the at least one of the plurality of dispensing events as at least one misappropriation event.

7. The computer-implemented method of claim 1, wherein the one or more dispensing logs identify at least one of: at least one employee of the plurality of users requesting dispensing of a drug, patient information, the drug being dispensed, an amount of the drug being dispensed, or wasting information.

8. The computer-implemented method of claim 1, wherein the one or more rules relate to determining, based on the plurality of dispensing events, at least one of: a certain type of drug, a drug quantity, or a wasting of a certain drug type over a threshold amount over a period of time.

9. A distributed analytics system for processing drug dispensing data to determine a possible drug misappropriation, the system comprising:

at least one processor; and at least one storage device storing instructions which, when executed by the at least one processor, cause the at least one processor to perform operations comprising:

receiving drug dispensing data from one or more data sources, the one or more data sources comprising at least one of: one or more dispensing logs or one or more electronic medical records (EMRs) received from a healthcare provider network;

identifying a plurality of dispensing events by a plurality of users based at least in part on the one or more dispensing logs;

detecting at least one drug misappropriation event corresponding to at least one of the plurality of dispensing events based on at least one of one or more rules or one or more drug dispensing patterns;

determining at least one confidence level corresponding to the at least one detected possible drug misappropriation, wherein the at least one confidence level is based on at least one of which of the one or more rules the at least one detected possible drug misappropriation satisfies, which of the one or more drug dispensing patterns to which the at least one detected possible drug misappropriation relates, or a level of deviation of the at least one detected possible drug misappropriation from the one or more drug dispensing patterns; and causing to display on an interface of a user device, by the distributed analytics system, an alert that includes:

detected possible drug misappropriation information of the at least one detected possible drug misappropriation and the at least one confidence level, and a feedback component for receiving feedback that enables activation or deactivation of a rule of the one or more rules or a pattern of the one or more drug dispensing patterns.

10. The computer system of claim 9, wherein the alert identifies a user of the plurality of users that dispensed the drug, a drug type, an drug amount, a wasting event, or prescription information.

11. The computer system of claim 9, the operations further comprising:

receiving, via the feedback component, feedback indicating whether the at least one detected possible drug misappropriation is an actual drug misappropriation.

12. The computer system of claim 11, wherein the feedback received via the feedback component activates or deactivates a rule of the one or more rules or a pattern of the one or more drug dispensing patterns.

13. The computer system of claim 4, wherein the feedback is received from a user using one or more graphical elements displayed on a graphical user interface.

14. The computer system of claim 9, wherein detecting the at least one misappropriation event corresponding to at least one of the plurality of dispensing events further includes:

determining that the at least one of the plurality of dispensing events falls outside of a standard deviation of the one or more drug dispensing patterns; and based on the determining, indicating the at least one of the plurality of dispensing events as at least one misappropriation event.

15. The computer system of claim 9, wherein the one or more dispensing logs identify at least one of: at least one employee of the plurality of users requesting dispensing of a drug, patient information, the drug being dispensed, an amount of the drug being dispensed, or wasting information.

16. The computer system of claim 9, wherein the one or more rules relate to determining, based on the plurality of dispensing events, at least one of: a certain type of drug, a drug quantity, or a wasting of a certain drug type over a threshold amount over a period of time.

17. A non-transitory computer readable medium storing instructions which, when executed by at least one processor of a distributed analytics system, cause the at least one processor to perform operations for processing drug dispensing data to determine a possible drug misappropriation, the operations comprising:

receiving drug dispensing data from one or more data sources, the one or more data sources comprising at least one of: one or more dispensing logs or one or more electronic medical records (EMRs) received from a healthcare provider network;

identifying a plurality of dispensing events by a plurality of users based at least in part on the one or more dispensing logs;

detecting at least one drug misappropriation event corresponding to at least one of the plurality of dispensing events based on at least one of one or more rules or one or more drug dispensing patterns;

determining at least one confidence level corresponding to the at least one detected possible drug misappropriation, wherein the at least one confidence level is based on at least one of which of the one or more rules the at least one detected possible drug misappropriation satisfies, which of the one or more drug dispensing patterns to which the at least one detected possible drug misappropriation relates, or a level of deviation of the at least one detected possible drug misappropriation from the one or more drug dispensing patterns; and causing to display on an interface of a user device, by the distributed analytics system, an alert that includes:

detected possible drug misappropriation information of the at least one detected possible drug misappropriation and the at least one confidence level, and a feedback component for receiving feedback that enables activation or deactivation of a rule of the one or more rules or a pattern of the one or more drug dispensing patterns.

18. The non-transitory computer readable medium of claim 17, the operations further comprising:

receiving, via the feedback component, feedback indicating whether the at least one detected possible drug misappropriation is an actual drug misappropriation.

19. The non-transitory computer readable medium of claim 18, wherein the feedback received via the feedback component activates or deactivates a rule of the one or more rules or a pattern of the one or more drug dispensing patterns.

20. The non-transitory computer readable medium of claim 17, wherein detecting the at least one drug misappropriation event corresponding to at least one of the plurality of dispensing events further includes:

determining that the at least one of the plurality of dispensing events falls outside of a standard deviation of the one or more drug dispensing patterns; and based on the determining, indicating the at least one of the plurality of dispensing events as at least one misappropriation event.

\* \* \* \* \*

UNITED STATES PATENT AND TRADEMARK OFFICE
CERTIFICATE OF CORRECTION

| | | |
|---|---|---|
| PATENT NO. | : 11,923,062 B2 | |
| APPLICATION NO. | : 18/172381 | |
| DATED | : March 5, 2024 | |
| INVENTOR(S) | : Nicholas T. Culbertson et al. | |

It is certified that error appears in the above-identified patent and that said Letters Patent is hereby corrected as shown below:

In the Claims

Column 32, Line 55, Claim 13, delete "claim 4" and insert --claim 9--.

Signed and Sealed this
Twenty-third Day of April, 2024

*Katherine Kelly Vidal*

Katherine Kelly Vidal
*Director of the United States Patent and Trademark Office*